US010849612B2

United States Patent
Harrison et al.

(10) Patent No.: US 10,849,612 B2
(45) Date of Patent: Dec. 1, 2020

(54) DEVICES AND METHODS FOR ADVANCING KNOTS

(71) Applicant: Anchor Orthopedics XT Inc., Mississauga (CA)

(72) Inventors: Robert Harrison, Milton (CA); Jeffery Arnett, Gilbert, AZ (US); Neil Godara, Milton (CA); Aye Nyein San, Mississauga (CA); Ilinca Popovici, Toronto (CA)

(73) Assignee: Anchor Orthopedics XT. Inc., Mississauga (CA)

( * ) Notice: Subject to any disclaimer, the term of this patent is extended or adjusted under 35 U.S.C. 154(b) by 630 days.

(21) Appl. No.: 14/759,217

(22) PCT Filed: Jan. 2, 2014

(86) PCT No.: PCT/IB2014/058026
§ 371 (c)(1),
(2) Date: Jul. 3, 2015

(87) PCT Pub. No.: WO2014/106822
PCT Pub. Date: Jul. 10, 2014

(65) Prior Publication Data
US 2015/0335325 A1 Nov. 26, 2015

Related U.S. Application Data

(60) Provisional application No. 61/748,796, filed on Jan. 4, 2013.

(51) Int. Cl.
*A61B 17/04* (2006.01)
*A61B 17/00* (2006.01)

(52) U.S. Cl.
CPC ...... *A61B 17/0469* (2013.01); *A61B 17/0483* (2013.01); *A61B 2017/00738* (2013.01);
(Continued)

(58) Field of Classification Search
CPC ............ A61B 17/0469; A61B 17/0483; A61B 2017/0474; A61B 2017/0496
See application file for complete search history.

(56) References Cited

U.S. PATENT DOCUMENTS

| 2,595,086 A | 4/1952 | Larzelere |
| 5,192,287 A * | 3/1993 | Fournier ............ A61B 17/0469 |
| | | 289/17 |

(Continued)

FOREIGN PATENT DOCUMENTS

| JP | H05192338 A | 8/1993 |
| WO | 9532671 A1 | 12/1995 |

(Continued)

OTHER PUBLICATIONS

Patent Corporation Treaty, International Search Report for PCT Application No. PCT/IB2014/058026 dated Apr. 3, 2014.
(Continued)

*Primary Examiner* — Julie A Szpira
(74) *Attorney, Agent, or Firm* — Vincent Man; Glenn Arnold; Samuel Tekie

(57) ABSTRACT

Embodiments of a knot pusher and methods of use thereof are disclosed, that are usable for pushing various types of knots including sliding knots and overhand knots formed from a suture, two limbs of the suture extending from the knots, for example using a single device. The knot pusher comprises a distal head defining top and bottom walls terminating in a distal knot pushing surface. The distal head includes side grooves that are defined between the top and bottom walls. Each of these side grooves are operable to receive one of the two limbs of suture during advancement of the distal head to aid in pushing the overhand knot. The distal head additionally comprises a suture receiving element associated with the top wall for receiving one of the (Continued)

two suture limbs during advancement of the distal head to facilitate advancement of the sliding knot.

20 Claims, 21 Drawing Sheets

(52) U.S. Cl.
CPC ............... *A61B 2017/00907* (2013.01); *A61B 2017/0474* (2013.01); *A61B 2017/0496* (2013.01)

(56) References Cited

U.S. PATENT DOCUMENTS

| | | | | |
|---|---|---|---|---|
| 5,320,629 | A * | 6/1994 | Noda | A61B 17/0469 606/113 |
| 5,397,326 | A * | 3/1995 | Mangum | A61B 17/0469 289/17 |
| 5,403,330 | A * | 4/1995 | Tuason | A61B 17/12013 606/139 |
| 5,405,352 | A * | 4/1995 | Weston | A61B 17/0469 289/1.2 |
| 5,439,470 | A * | 8/1995 | Li | A61B 17/0469 289/17 |
| 5,601,576 | A * | 2/1997 | Garrison | A61B 17/0469 606/139 |
| 5,653,719 | A | 8/1997 | Raiken | |
| 5,752,964 | A | 5/1998 | Mericle | |
| 5,759,189 | A * | 6/1998 | Ferragamo | A61B 17/0469 606/139 |
| 6,010,515 | A * | 1/2000 | Swain | A61B 1/00089 600/104 |
| 6,132,439 | A | 10/2000 | Kontos | |
| 7,981,125 | B1 * | 7/2011 | Colvin | A61B 17/0467 606/148 |
| 8,202,282 | B2 | 6/2012 | Schmieding et al. | |
| 2007/0219567 | A1 | 10/2007 | Bayer et al. | |
| 2008/0140092 | A1 * | 6/2008 | Stone | A61B 17/0401 606/144 |
| 2011/0022083 | A1 * | 1/2011 | DiMatteo | A61B 17/0401 606/228 |
| 2011/0087284 | A1 * | 4/2011 | Stone | A61B 17/0401 606/232 |

FOREIGN PATENT DOCUMENTS

| | | |
|---|---|---|
| WO | 9812970 A1 | 4/1998 |
| WO | 0215795 A2 | 8/2000 |

OTHER PUBLICATIONS

Patent Corporation Treaty, Written Opinion for PCT Application No. PCT/IB2014/058026 dated Apr. 2, 2014.
Patent Corporation Treaty, International Preliminary Report on Patentability, PCT Application No. PCT/IB2014/058026, dated Jul. 7, 2015.
Corresponding European Application, European Search Opinion, dated Aug. 10, 2016.
Corresponding European Application, Supplementary European Search Report, dated Aug. 1, 2016.
Corresponding European Application, Communication Pursuant to Article 94(3) EPC, dated Feb. 9, 2018.
Corresponding European Application, Communication Pursuant to Article 94(3) EPC, dated Jan. 18, 2019.
Corresponding Japanese Application, Office Action, dated Sep. 5, 2018.
Corresponding Japanese Application, Office Action, dated Apr. 24, 2019.
Related Application, Patent Corporation Treaty, International Search Report for PCT Application No. PCT/IB2014/062988, dated Nov. 3, 2014.
Related Application, Patent Corporation Treaty, Written Opinion for PCT Application No. PCT/IB2014/062988, dated Oct. 28, 2014.
Related Application, Patent Corporation Treaty, International Preliminary Report on Patentability, PCT Application No. PCT/IB2014/062988, dated Jul. 5, 206.
Related European Application, European Search Opinion, dated Jul. 28, 2017.
Related European Application, Supplementary European Search Report, dated Jul. 19, 2017.
Related European Application, Communication pursuant to Art 94(3) EPC, dated Jan. 4, 2019.
Related European Application, Communication pursuant to Art 94(3) EPC, dated Oct. 30, 2019.
Related Japanese Application, Office Action, dated Jun. 27, 2018.
Related US Application, Non-Final Rejection, dated Apr. 19, 2019.
Related US Application, Final Rejection, dated Jan. 24, 2020.
Related US Application, Non-Final Rejection, dated May 8, 2020.

* cited by examiner

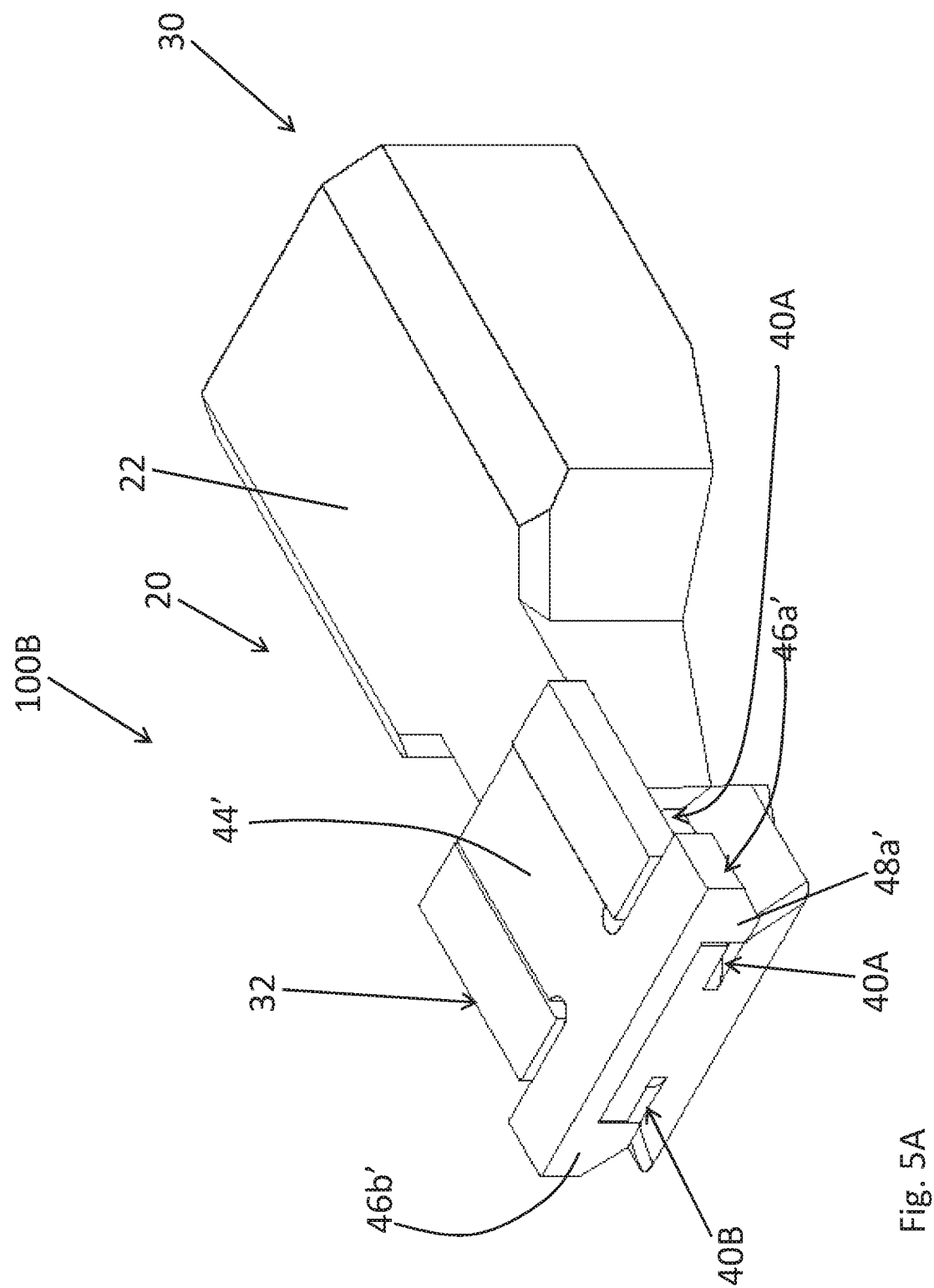

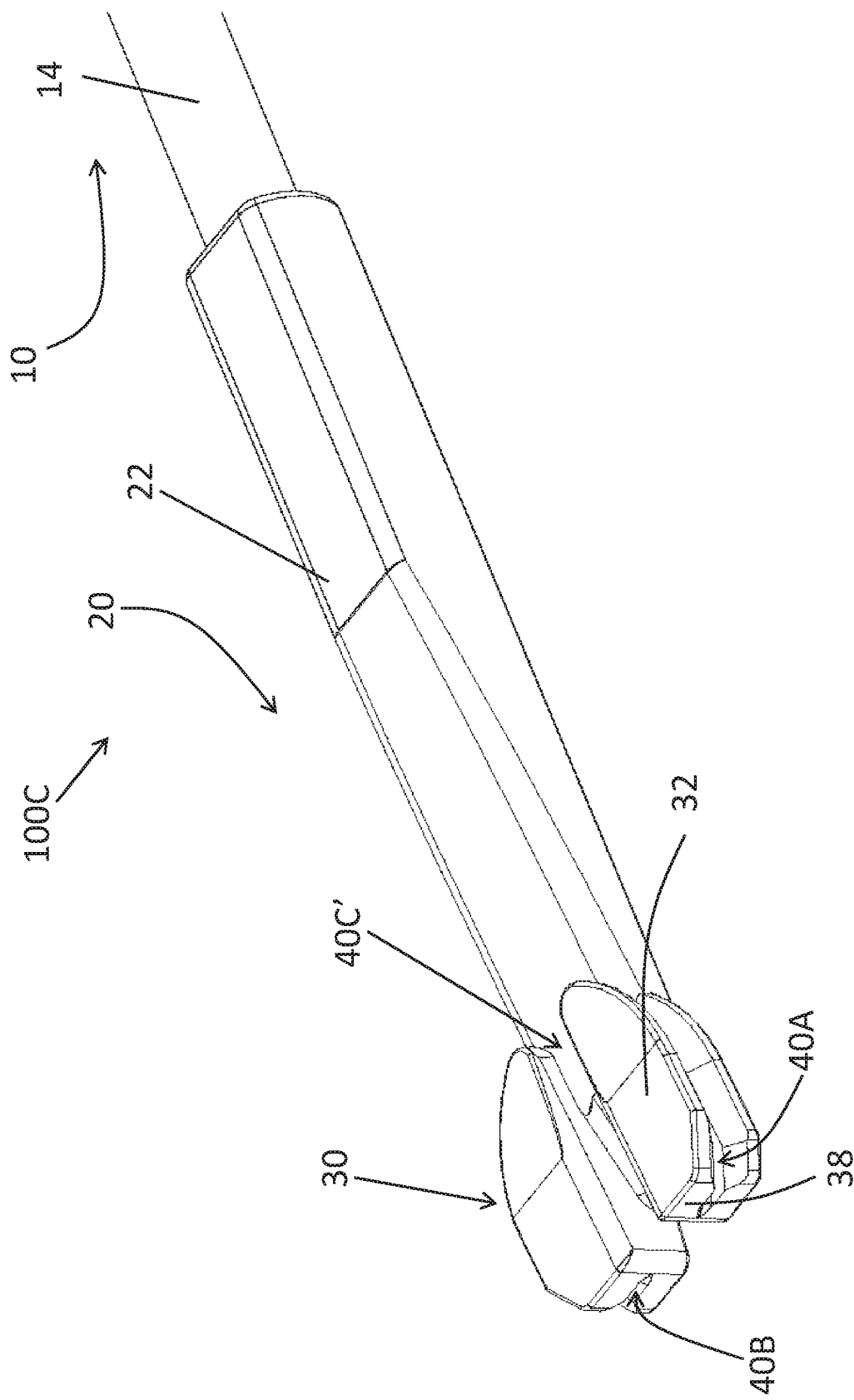

DEVICES AND METHODS FOR ADVANCING KNOTS

TECHNICAL FIELD

The disclosure relates to a medical device, more specifically to a knot pusher.

SUMMARY

In one broad aspect, embodiments of the present invention comprise a knot pusher usable for pushing various types of knots including sliding knots and overhand knots formed from a suture, two limbs of the suture extending from the knots, the knot pusher comprising: a distal head defining top and bottom walls terminating in a distal knot pushing surface; side grooves defined between said top and bottom walls, said side grooves extending proximally from said knot pushing surface along said distal head, each operable to receive one of the two limbs of suture during advancement of said distal head to aid in pushing said overhand knot; and a suture receiving element associated with said top wall for receiving one of the two suture limbs during advancement of said distal head to facilitate advancement of said sliding knot.

In another broad aspect, embodiments of the present invention comprise a knot pusher for pushing an overhand knot formed from a suture, two limbs of the suture extending from the knot, the knot pusher comprising: a distal head defining top and bottom walls terminating in a distal knot pushing surface; side grooves defined between said top and bottom walls, said side grooves extending proximally from said knot pushing surface along said distal head, each operable to receive one of the two limbs of suture during advancement of said distal head to aid in pushing said overhand knot; and at least one suture retaining element for retaining a suture limb within at least one of said side grooves to prevent disengagement of said one of the suture limbs from the knot pusher during advancement of the distal head to push said overhand knot.

In another broad aspect, embodiments of the present invention comprise a method for advancing a sliding knot and one or more overhand knots to a tissue site within a patient's body, the tissue site comprising tissue defining a defect, each of said knots formed from a suture, two limbs of the suture extending from the knot, the method utilizing a single device to advance the sliding knot and the one or more overhand knots, the method comprising the steps of: advancing the sliding knot to the tissue site by applying force to the sliding knot using the device; and advancing each of the one or more overhand knots to the tissue site by applying force to the overhand knot using the device while retaining the two suture limbs along opposite sides of the device; whereby an angle between the two suture limbs at a distal end of the device is about 180 degrees for applying a substantially lateral force to the two suture limbs as the overhand knot is tightened.

In an additional broad aspect, embodiments of the present invention comprise a method for advancing one or more overhand knots to a tissue site within a region of tissue within the patient's body, each of said knots formed from a suture, two limbs of the suture extending from the knot, the method comprising the steps of: receiving the two suture limbs along opposing sides of the overhand knot to permit the two suture limbs to be separated by about 180 degrees; and advancing the overhand to the tissue site by applying a force against the overhand knot to position the overhand knot at the tissue site.

In still another broad aspect, embodiments of the present invention comprise a method of advancing a sliding knot and one or more overhand knots, said sliding knot for substantially securing a suture loop passed around a defect within an intervertebral disc, the method utilizing a single device to advance the sliding knot and the one or more overhand knots, the method comprising the steps of: advancing the sliding knot to the defect site by applying a force to the sliding knot using the device, in order to approximate the tissue at the site of the defect; and advancing each of the one or more overhand knots to the defect site by applying a force to the overhand knot using the device to position the overhand knot adjacent the sliding knot at the tissue site to secure the sliding knot.

In still another broad aspect, embodiment of the present invention comprise a knot pusher usable for pushing various types of knots formed from a suture, including sliding knots and overhand knots, two suture limbs extending from the knots, the knot pusher comprising: a distal head comprising top and bottom walls terminating in a distal knot pushing surface; a handle coupled to said distal head via a shaft, for advancing said distal head to push knots; a pair of spaced apart laterally opposed side grooves defined between said top and bottom walls, each of said pair of side grooves extending proximally from said knot pushing surface along said distal head, each for receiving one of the two suture limbs during advancement of said distal head to aid in pushing an overhand knot; and an intermediate groove associated with said top wall between said pair of opposed side grooves, said intermediate groove extending proximally from said knot pushing surface longitudinally along said distal head, for holding one of the two suture limbs during advancement of said distal head to facilitate advancement of a sliding knot.

BRIEF DESCRIPTION OF THE DRAWINGS

In order that the invention may be readily understood, embodiments of the invention are illustrated by way of examples in the accompanying drawings, in which:

FIGS. 5A-5B illustrate an alternate embodiment of a knot pusher in accordance with the present invention;

FIGS. 6A-6C illustrate a still further alternative embodiment of a knot pusher in accordance with the present invention;

DETAILED DESCRIPTION

Figure 1A:
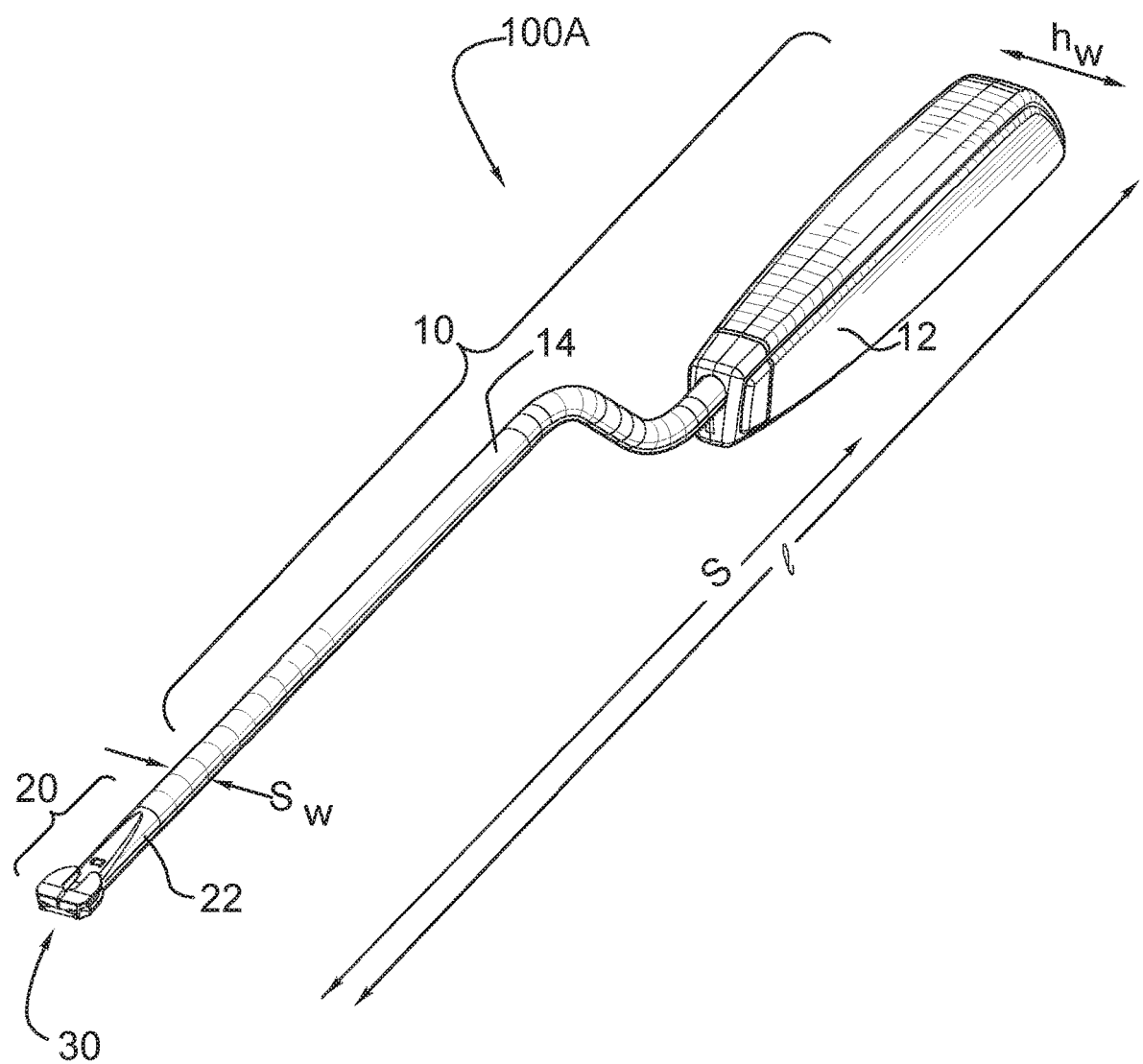
FIG. 1A illustrates a top, front perspective view of a knot pusher in accordance with an embodiment of the present invention.

In one broad aspect, embodiments of the present invention provide a means for advancing and tightening a knot formed in a suture at a site within a region of tissue of a patient's body. In some applications, this may be taken to include a site that is on a surface of a patient's body. In alternate applications, the site may be remote or within a region of tissue to which access is limited or restricted. Such applications particularly warrant the use of a knot pusher to advance and tighten the knot.

In some applications it may be desirable to apply a sliding knot in order to secure the suture. In a particular example, a sliding knot may be deployed after delivery of suture through a region of tissue at the site of a defect, for example at an annulus fibrosis of an intervertebral disc. In some such examples, access to the intervertebral disc may be provided through a portal, inserted for example through a lamina of a vertebra, to allow the suture to be passed through to the affected disc. A sliding knot may then be deployed to secure the suture.

In such situations, since access to the intervertebral disc is restricted, a knot pusher may be utilized to advance the sliding knot through the portal towards the site of the defect. The knot pusher may allow for advancement of the sliding knot and may further enable initial approximation of the tissue at the defect. The knot pusher may additionally be used to tighten and lock the sliding knot. Oftentimes, in order to further reinforce the sliding knot, the physician desires to apply one or more additional half-hitches or overhand knots over the sliding knot. These may help ensure that the sliding knot does not open or unravel after the procedure. The mechanism/procedure for pushing and tightening the knot is different for both sliding knots and overhand knots and advancing these different types of knots typically requires use of a plurality of knot pushers, each designed for a particular type of knot.

The present inventors have discovered and reduced to practice several embodiments of a knot pusher for pushing both sliding knots and overhand knots. Pushing both a sliding knot and an overhand knot in a medical procedure using the same device is achieved, for example, by providing a knot pusher having a suture receiving element, such as an intermediate groove, for holding one of the two limbs of the suture forming the sliding knot to allow the knot pusher to push the sliding knot. The knot pusher additionally has opposed side grooves for receiving, holding or guiding one or both limbs of the suture forming an overhand knot to allow the knot pusher to push the overhand knot.

In some embodiments, the knot pusher comprises features to facilitate suture engagement with the knot pusher and to reduce the operating time. In one specific example, the knot pusher has at least one suture retaining element to retain a limb of the suture within one of the side grooves to prevent disengagement of the suture limb from the knot pusher during advancement of the distal head to push the overhand knot.

Such embodiments are particularly useful and advantageous, for example, when there is limited access to the tissue site where the knots are being deployed. Embodiments of the present invention avoid the use of multiple devices to deploy different types of knots, and as such reduces the number of devices that need to be utilized to complete the procedure. Furthermore, embodiments of the present invention provide a device that enables both effective and efficient delivery of different types of knots to the desired tissue location without disengagement of the suture from the device.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In accordance with an embodiment of the present invention, and as shown in FIG. 1A, a knot pusher 100A is disclosed for advancing a knot formed in a suture to a site within a patient's body and for additionally tightening the knot. In some embodiments, the knot pusher 100 allows a knot to be advanced to a site that may be remote or within a region of tissue to which access is limited or restricted, the knot terminating in two strands of suture.

As used herein, the phrases "two strands of suture", "two ends of suture", "two limbs of suture" and variations thereof, are interchangeable and refer to the portions of suture exiting/deriving from/outside a suture knot, i.e. the portions of suture that are not constrained by the knot. Typically, these portions are parts of a single strand or thread of suture. Although the term '"end" of suture' is used, in this context it should be understood to refer to that portion of the suture exiting the knot, rather than to the actual physical end of the suture strand.

In addition, it should be understood that the term strand as used herein refers to a portion of suture regardless of the number of filaments included therein (i.e. both monofilament and multifilament sutures or portions thereof are referred to as a strand of suture).

In some portions of the description below, and as would be understood by one of skill in the art based on the context, a 'strand' of suture may refer to either the working part, standing part or both the working and standing part of the knot construct. In some such embodiments the two strands or limbs exiting the knot are understood to be the standing part of the suture and the part of the suture forming the knot that is used to retain the suture is understood to be the working part of the suture.

Figure 1B:
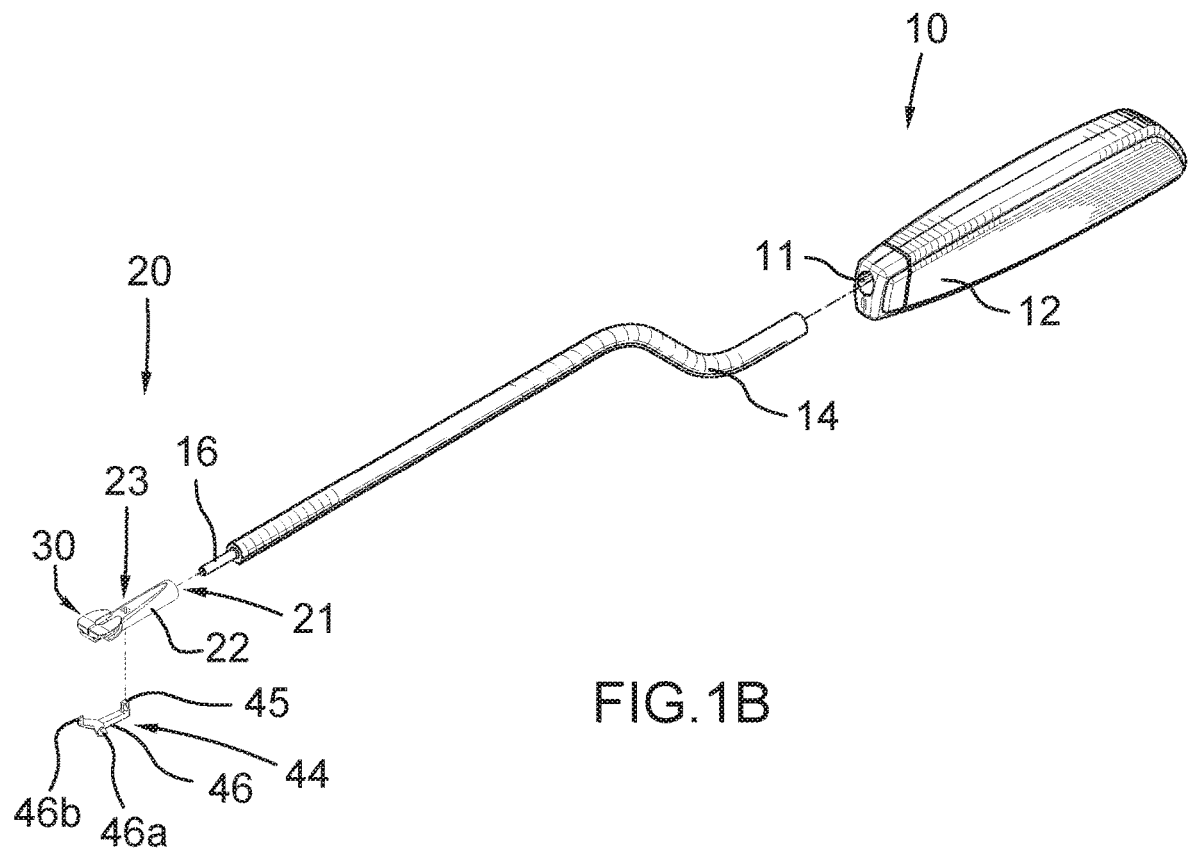
FIG. 1B illustrates an exploded view of a knot pusher in accordance with an embodiment of the present invention.
Figure 1C:
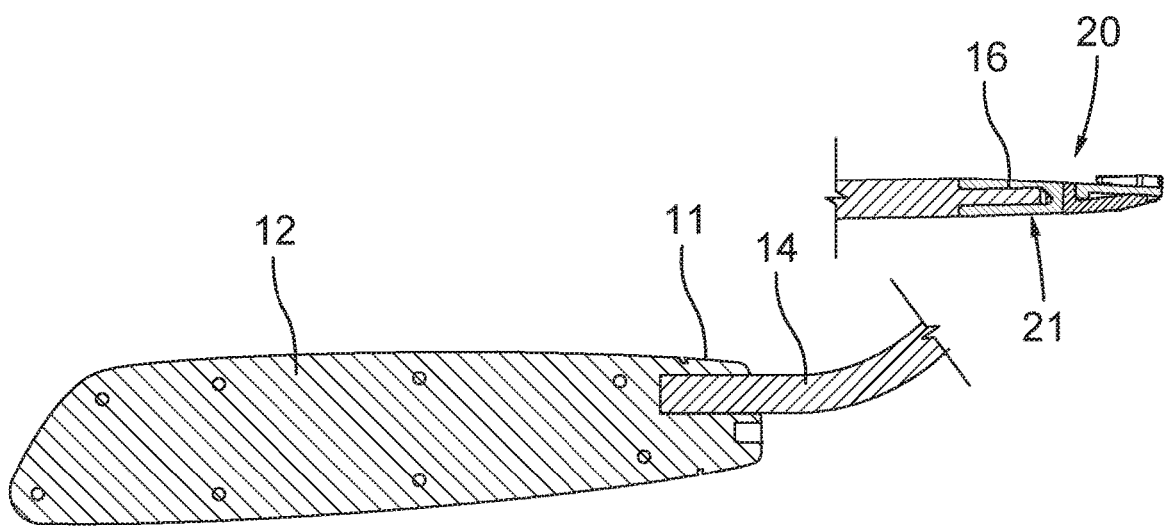
FIG. 1C illustrates a right side cross-sectional view of proximal and distal portions of a knot pusher in accordance with an embodiment of the present invention.

As shown in FIG. 1A, the knot pusher 100A comprises a proximal portion 10 that is coupled to a distal portion 20. The proximal portion 10 comprises a handle 12 that is coupled to the distal portion 20 via an elongated shaft 14 (of the proximal portion 10). The handle 12 is operable to exert a force along the elongated shaft 14 that is transmitted to the distal portion 20 for pushing the knot. In one specific example, as shown in FIGS. 1B and 1C, the shaft 14 co-operatively engages with the handle 12. For example, the shaft 14 is received within and fits within a recess 11 within the handle 12. Additionally, the shaft 14 may be secured within the recess 11 using an adhesive, such as a Loctite® 4011 adhesive.

The distal portion 20 further comprises a distal head 30 that is coupled to the elongated shaft 14 via a neck portion (or simply "neck") 22 formed within the distal portion 20. In one specific example, as shown in FIGS. 1B and 1C, the shaft 14 comprises a peg or protrusion 16 that is received within a recess 21 within the distal portion 20 and co-operatively engages therewith. In one specific example, the peg 16 may be secured within the recess 21 using an adhesive, such as Loctite® 4011 adhesive. The distal head 30 interacts with the knot, as well as one or more strands of suture coupled to the knot during advancement of the distal portion 20, to advance and tighten the knot at the desired tissue site. In other embodiments the distal head 30 may be coupled directly to the shaft 14 without the use of an intermediate neck portion 22. In some examples, the neck portion 22 may be a part of the shaft 14. In other embodiments, the distal head 30 may be detachably coupled to the shaft 14 or the neck portion 22. This may permit the distal head 30 to be formed as a single-use component whereas the shaft 14 and the handle 12 may be reusable and may be sterilizable to permit multiple uses. In still further examples, the distal head 30 may be provided in various sizes and may be customizable for use in different areas in the body or to accommodate various sizes of sutures or different types of knots.

Figure 1D:
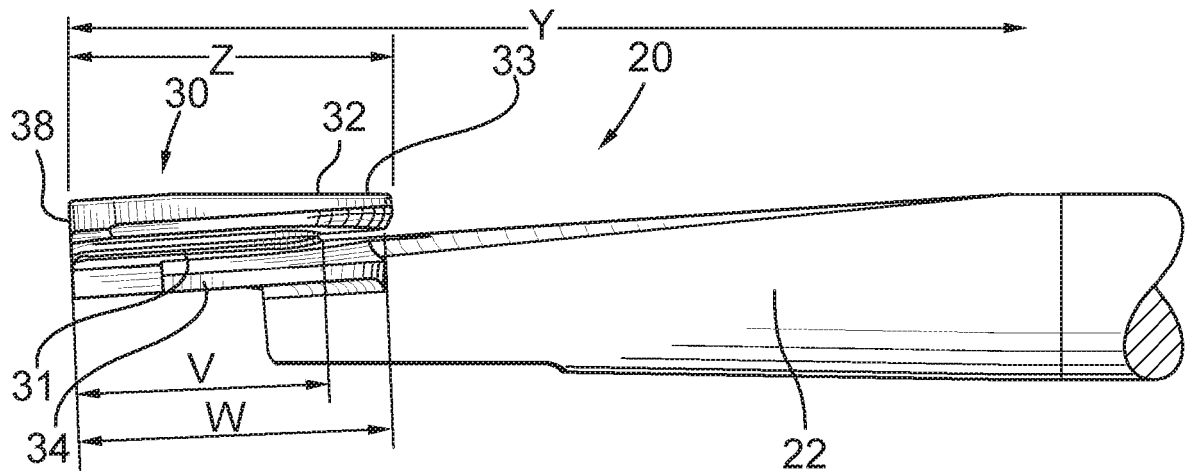
FIG. 1D illustrates a left side view of a distal portion of a knot pusher in accordance with an embodiment of the present invention.
Figure 1E:
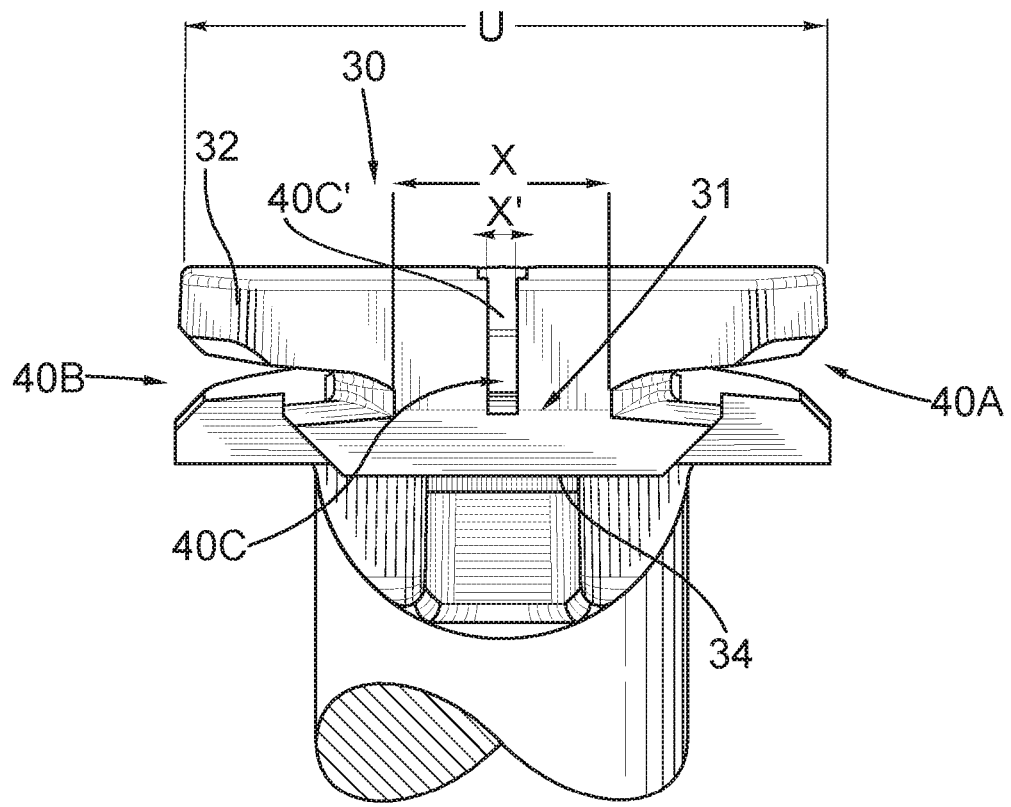
FIG. 1E illustrates a front end view of a distal portion of a knot pusher in accordance with an embodiment of the present invention.
Figure 2:
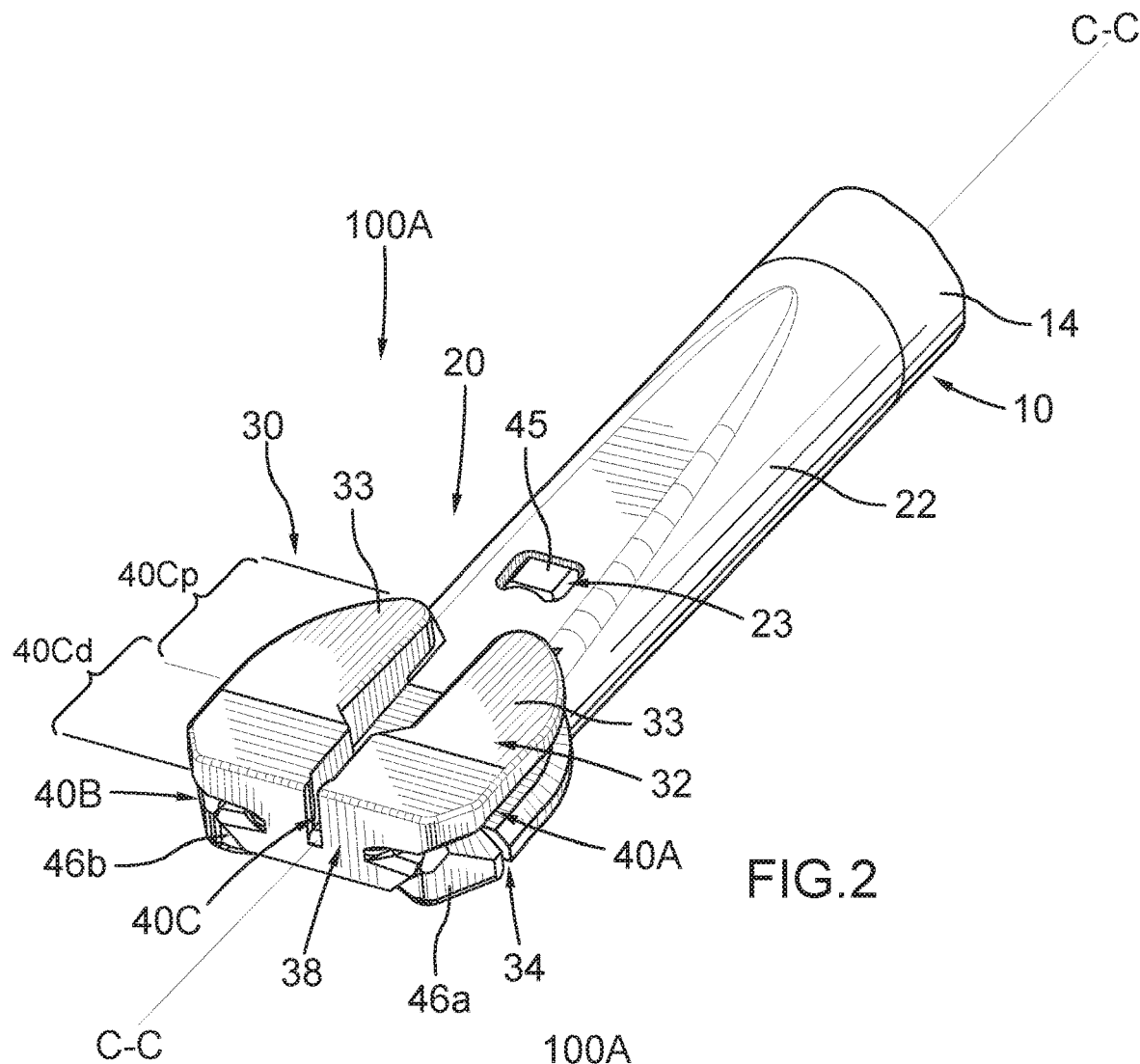
FIG. 2 illustrates a top front perspective view of a distal portion of knot pusher in accordance with an embodiment of the present invention.
Figure 3:
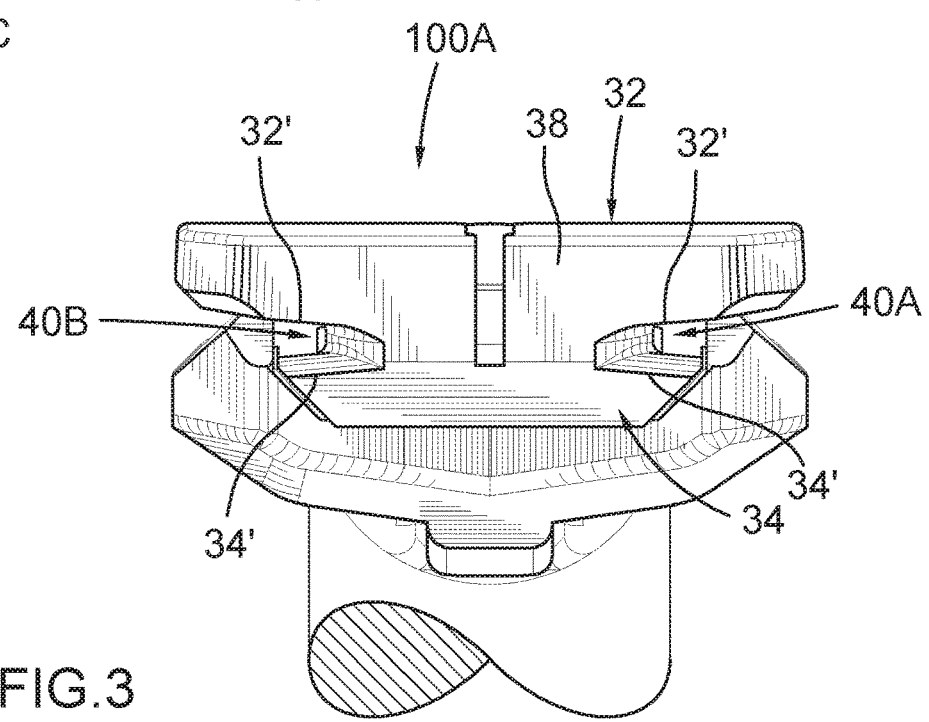
FIG. 3 shows a front view of a distal portion of knot pusher in accordance with an embodiment of the present invention.

With reference now to FIG. 1D, the distal head 30 comprises top and bottom walls (or faces) 32, 34 (which may alternatively be referred to as upper and lower walls or faces 32,34) respectively that terminate in a distal knot pushing surface 38 that interacts directly with the knot to push the knot distally. The distal knot pushing surface 38 is visible in FIG. 1E that shows a front view of the distal head 30. In some embodiments, the distal knot pushing surface 38 is a substantially flat planar surface. In some embodiments, the bottom wall 34 is formed integrally with the neck 22 and is planarly offset from the top wall 32, as seen in FIGS. 1D-1E and 2. In other words, the top and bottom walls 32, 34 are along separate planes that are offset, but possibly parallel, relative to one another. Additionally, as shown in FIG. 3, the top and bottom walls 32, 34, define two laterally opposed side grooves 40A and 40B, extending between the respective inner surfaces 32' and 34' of each of the top and bottom walls 32, 34. Each of the side grooves 40A and 40B are designed to receive, hold, contain or retain at least one of the two strands of suture extending or deriving from a knot. In one example, the top and bottom walls 32, 34 are chamfered to facilitate the loading of the suture within the side grooves 40A, 40B. In some embodiments, the side grooves are continuous, i.e. a single continuous groove extends along both sides as well as along the knot pushing surface 38.

Furthermore, as shown in FIGS. 1D and 1E, a portion of each of the top and bottom walls 32 and 34 may be joined along a longitudinal axis of the distal head 30, defining a support 31' that extends along the longitudinal axis and is positioned transversally between the longitudinally extending side grooves 40A and 40B. The support 31' is defined as a region or component of the distal head 30 that connects the top and bottom walls 32, 34 so that they are connected to or integral with one another along the longitudinal axis of the distal head 30. In one particular example, as shown, the distal head 30 comprises a central support 31 that connects the top and bottom walls 32, 34 such that are connected along the central axis of the distal head 30. The side grooves 40A and 40B do not extend transversally along the central support 31. Therefore, the side grooves 40A and 40B are spaced apart laterally from one another by a fixed distance that may be equal to the width of the central support 31. This forces the two suture strands of an overhand knot, each positioned in one of the side grooves 40A and 40B, to spread apart as the knot is being pushed and/or advanced. The grooves 40A and 40B are distanced from one another to enable the two suture strands to be oriented at an angle of about 180° with respect to the overhand knot along the knot pushing surface 38 and with respect to one another, to permit effective tightening and locking of the overhand knot. The further the side grooves 40A and 40B are spaced apart from one another, the closer the respective angle between the two suture strands is to 180 degrees. In some embodiments, the distance between the side grooves 40A and 40B is related to the width of the side grooves 40A, 40B and in some embodiments this distance may also relate to the width of the suture to be used with the knot pusher. In one particular embodiment, the side grooves 40A and 40B are spaced apart by a distance that is equal to about 10 times the diameter of the suture being used which may be, for example, substantially equivalent to the width of each of the two side grooves 40A, 40B. In one specific example, the distance between the side slots for a 2-0 suture may be about 0.110".

As shown in FIG. 1E and FIG. 2, the knot pusher 100A additionally comprises a suture receiving element, for example associated with the top wall of the distal head, i.e. a top wall suture receiving element. The top wall suture receiving element may be, for example, a component able to receive a limb of a suture such as a 'gun sight'-type structure which has two side walls protruding from the top wall and defining a gap or groove into which a suture may be received. Alternatively, as illustrated in FIG. 1E and FIG. 2, the suture receiving element comprises an intermediate groove 40C formed within the top wall or face 32 that extends proximally from the knot pushing surface 38 and extends longitudinally along the top wall 32. The intermediate groove 40C opens into the top face 32. More specifically, in some embodiments, the intermediate groove 40C may be formed within the support 31' such as the central support 31 as described above. In some embodiments, the intermediate groove 40C may be formed within the top wall 32 but may extend (in depth) into a portion of the bottom wall 34. The intermediate groove 40C is thereby in communication with the knot pushing surface 38 and terminates at the knot pushing surface 38. The intermediate groove 40C allows one of the two strands of suture exiting a sliding knot to be held therein as the knot pusher 100A is advanced to push the sliding knot using the knot pushing surface 38.

In some embodiments, at least a portion of the intermediate groove 40C, for example at least along a distal portion thereof, such as portion 40Cd, has a width smaller than that of the knot to prevent the knot from sliding into the groove as the knot pusher 100 is advanced distally to push the knot. More specifically, the intermediate groove 40C allows a post (as discussed with reference to FIG. 7) of the sliding knot to be positioned or received within the intermediate groove 40C while the knot pusher 100A is advanced to push the sliding knot against the tissue.

Figure 1F:
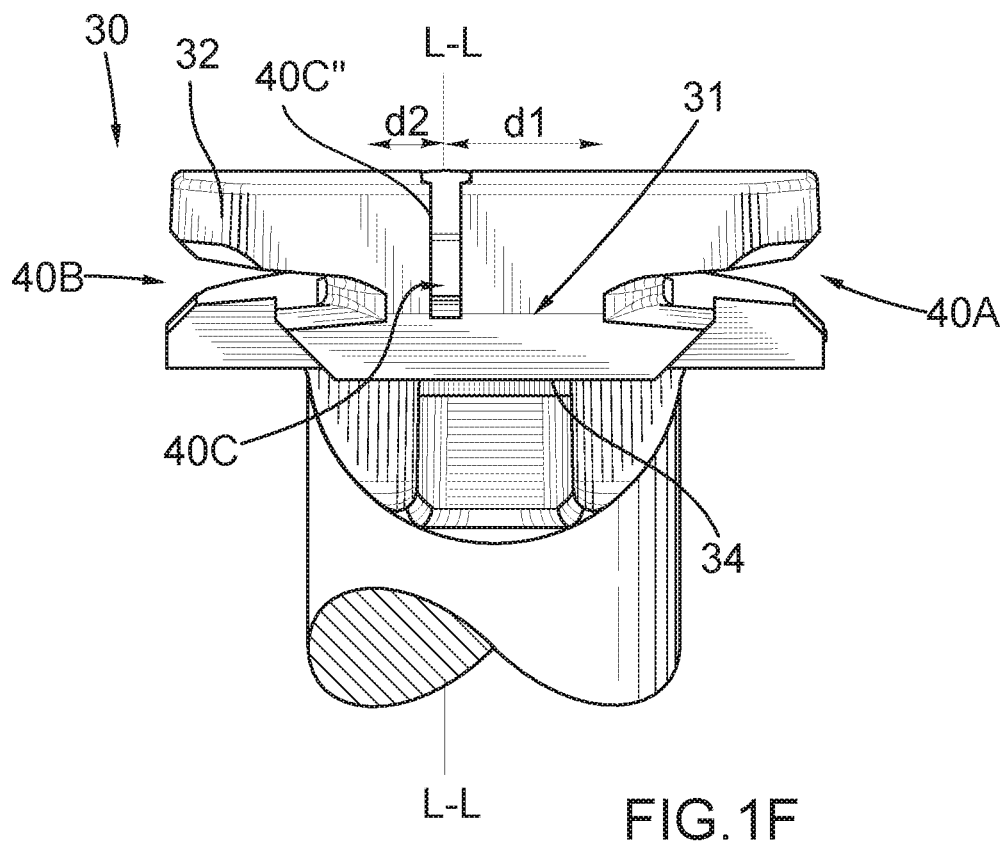
FIGS. 1F-1I, each illustrate a front end view of a distal portion of a knot pusher in accordance with an alternate embodiment of the present invention.

In some embodiments, the intermediate groove 40C may extend along the central support 31 and may be positioned equidistant from the side grooves 40A, 40B forming a central groove 40C' along a central axis C-C of the knot pusher 100A, as shown in FIGS. 1E and 2. The configuration of the intermediate groove 40C facilitates advancement of a sliding knot. In alternate embodiments, the intermediate groove 40C may be transposed laterally along the central support 31 and may be positioned relatively closer to one of the side grooves as compared to the other side groove, as shown in FIG. 1F. In other words, the intermediate groove 40C may extend along a longitudinal axis L-L of the distal head that is parallel to and offset from the central axis C-C, forming an offset groove 40C". For example, as shown in FIG. 1F, the offset groove 40C" is positioned closer to the side groove 40A, when compared to side groove 40B. More specifically, the offset groove 40C" is positioned at a distance d1 from side groove 40A, and at a distance d2 from side groove 40B, where d1 is less than d2. The present configuration of an offset groove 40C" also facilitates advancement of a sliding knot 82.

In one specific example, the central groove or channel 40C, in addition to facilitating advancement or pushing of the sliding knot, functions as a viewing channel to facilitate advancement and tightening of the overhand knot. In other words, the intermediate groove 40C permits viewing of the overhand knot as it is being tightened in order to maintain equal tension on both strands of suture. If unequal tension is applied to the knot it may not remain centered at the tip of the knot pusher and may no longer be visible to the user through the intermediate groove 40C. Thus, the intermediate groove 40C allows the user to maintain visualization of the overhand knot as it is being pushed to ensure that the overhand knot is correctly positioned and is tightened adequately and effectively at the desired target tissue surface. In some embodiments, the intermediate groove 40C allows visualization of the overhand knot to help ensure that it is positioned adjacent and over top of the sliding knot at the desired tissue surface. In some embodiments, at least a proximal portion of the intermediate groove 40C, such as portion 40Cp shown in FIG. 2, has a width that is greater than the width of the suture or suture knot to further enhance visualization of the overhand knot. As shown in FIG. 2, in some such embodiments, the width of the intermediate groove 40C may vary along its length. In further embodiments, in order to facilitate visualization of the sliding and/or overhand knots as well as the placement of the strands of suture into any of the grooves 40A, 40B and 40C, the distal head 30 may be translucent and may comprise a material that is clear or transparent. As such the transparent distal head 30 may enhance the ease of use of the knot pusher 100A and may facilitate advancement and placement of sliding and overhand knots within a desired tissue location within a patient's body. Additionally, the distal head 30 may comprise marking thereon indicating where the strands may be placed and in which order to facilitate advancement of sliding and overhand knots.

Figure 1G:
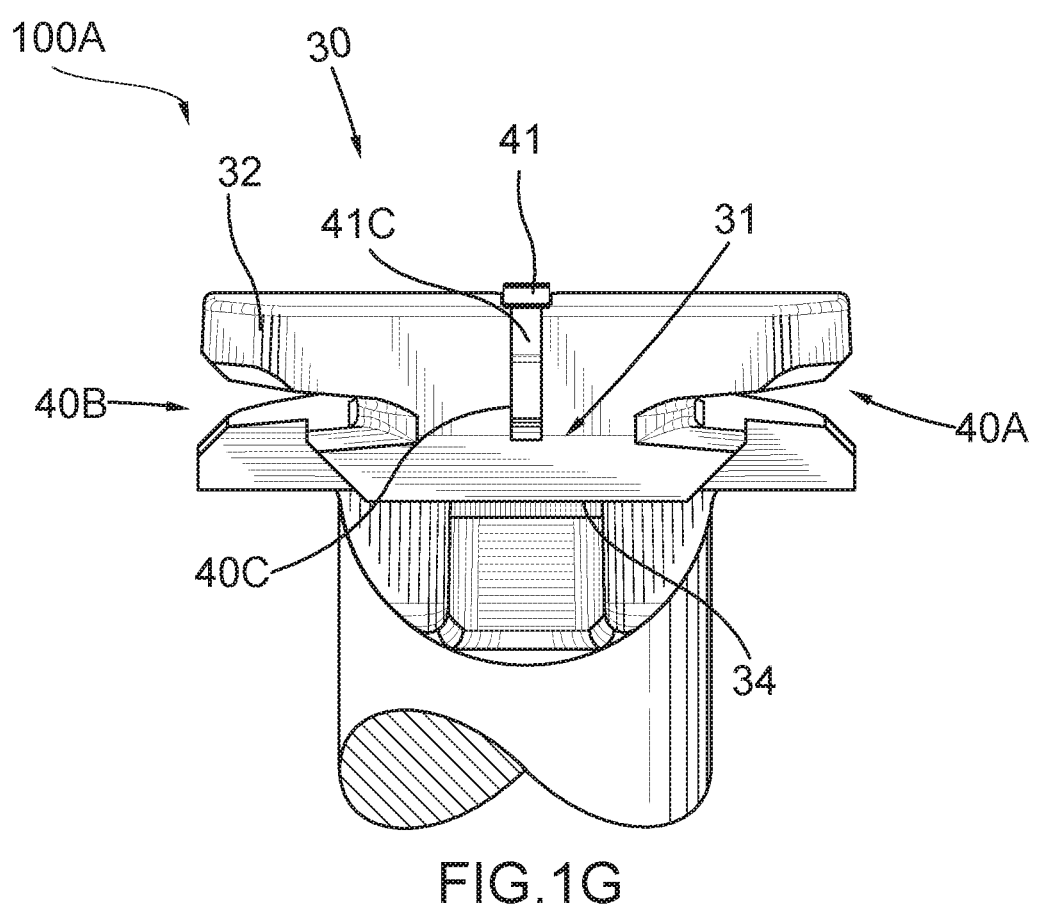

In still another embodiment, as shown in FIG. 1G, the groove 40C may be a covered with a cover or cap 41 that encloses the groove 40C at least partially along its length, forming a tunnel or enclosed groove 41C. In some embodiments, the cap 41 may be formed integrally with the groove 40C. Thus, enclosed groove 41C comprises the intermediate groove 40C and the cap 41 that encloses the intermediate groove 40C. The enclosed groove 41C may allow suture to be threaded there-through to be held therein to prevent detachment of the suture during use as the knot pusher 100A is being advanced to position the sliding knot at the desired target location within tissue within a patient's body. As such the enclosed groove 41C may prevent the suture from sliding out, for example when force is applied against a sliding knot by the distal head 30 when the knot pusher 100A is advanced.

Figure 1H:
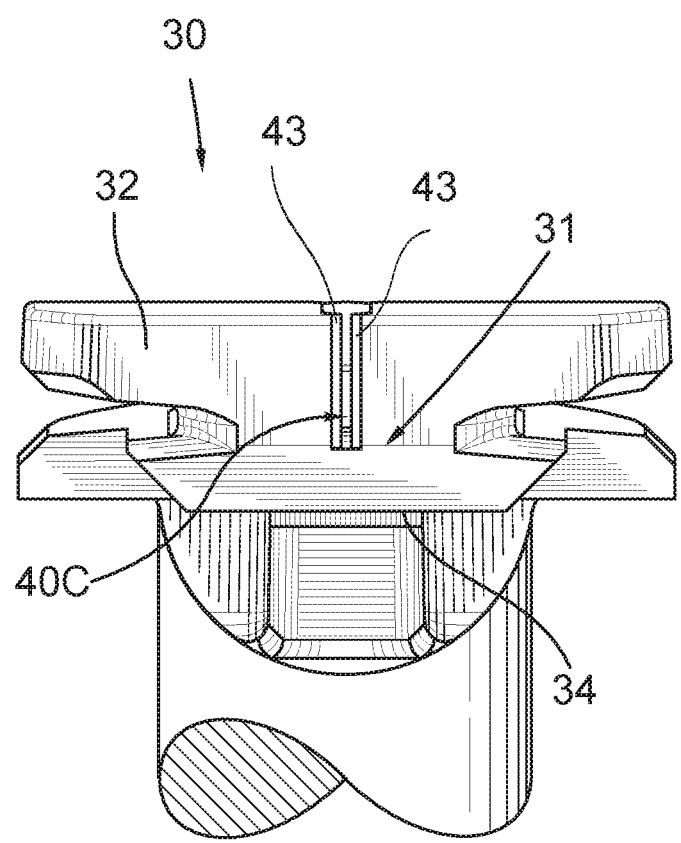

In further embodiments, as illustrated in FIG. 1H, the distal head 30 of the knot pusher 100A may additionally comprise a suture retention feature for retaining the suture within the intermediate groove 40C. For example the intermediate groove 40C may comprise a suture retention feature comprising a suture retaining element that extends at least partially along its length. In one particular example, a resilient material 43 may be positioned within the intermediate groove 40C, for example, on the inside of the intermediate groove 40C, along one or more inner walls of the intermediate groove 40C. In a particular example as shown, the resilient material 43 is positioned on the inside of the intermediate groove 40C along both of the inner walls of the intermediate groove 40C, and effectively narrows a channel formed within the intermediate groove 40C. The resilient material 43 in its nominal position or closed position functions to partially block the opening or passage of the intermediate groove 40C thereby narrowing its width. As the suture is inserted within the intermediate groove 40C, the resilient material flexes from its nominal or closed position to an open position thereby widening the channel within the intermediate groove 40C, to allow a strand of suture to be received within the intermediate groove 40C. Thereafter, the resilient material returns to its nominal or closed position to retain the suture within the intermediate groove 40C.

In alternative embodiments, the intermediate groove 40C may comprise one or more resilient snap arms to retain the suture which may function similarly to snap arms described herein below with respect to the side grooves 40A, 40B. The snap arms may extend inwardly into the intermediate groove 40C. The snap arm may initially block entry of the suture into the intermediate groove 40C but have the ability to flex to allow the suture to be passed into the intermediate groove 40C. After the suture is placed into the intermediate groove 40C, the snaps arms may then return their original position trapping the suture within the channel of the intermediate groove 40C preventing it from slipping out during use.

In still a further embodiment, the intermediate groove 40C could comprise a suture retaining element or component in the form of a moveable cap. For example, cap 41, as discussed previously, could be moveable and operatively coupled in a sliding arrangement with the intermediate groove 40C thereby allowing suture to be inserted in its open configuration and retaining or trapping the suture in a closed configuration. The cap may be closed, for example, by sliding it over the groove 40C. In other embodiments, the suture retaining element may be in the form of a sliding pin that functions to retain the suture in its closed configuration while allowing free passage of the suture into the groove in its open configuration. Still furthermore, in an alternative example, the suture retaining element comprises a latch.

Figure 1I:
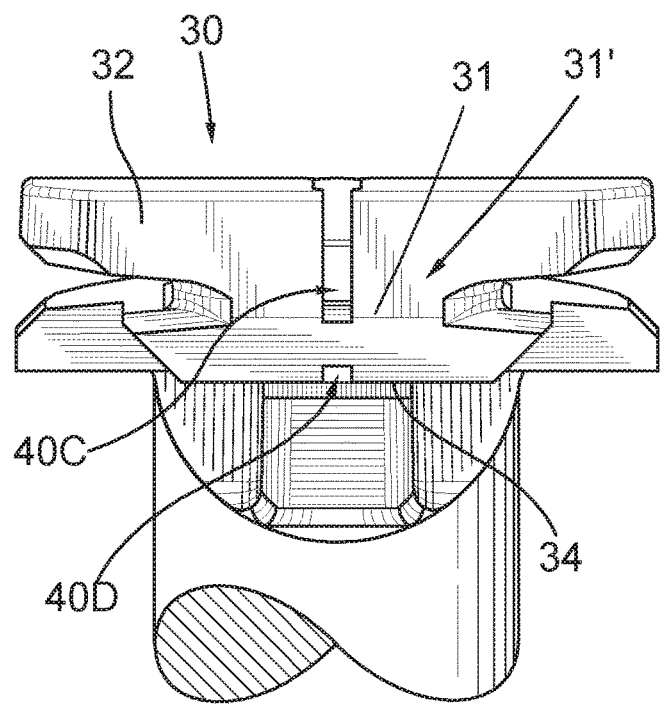
Figure 1J:
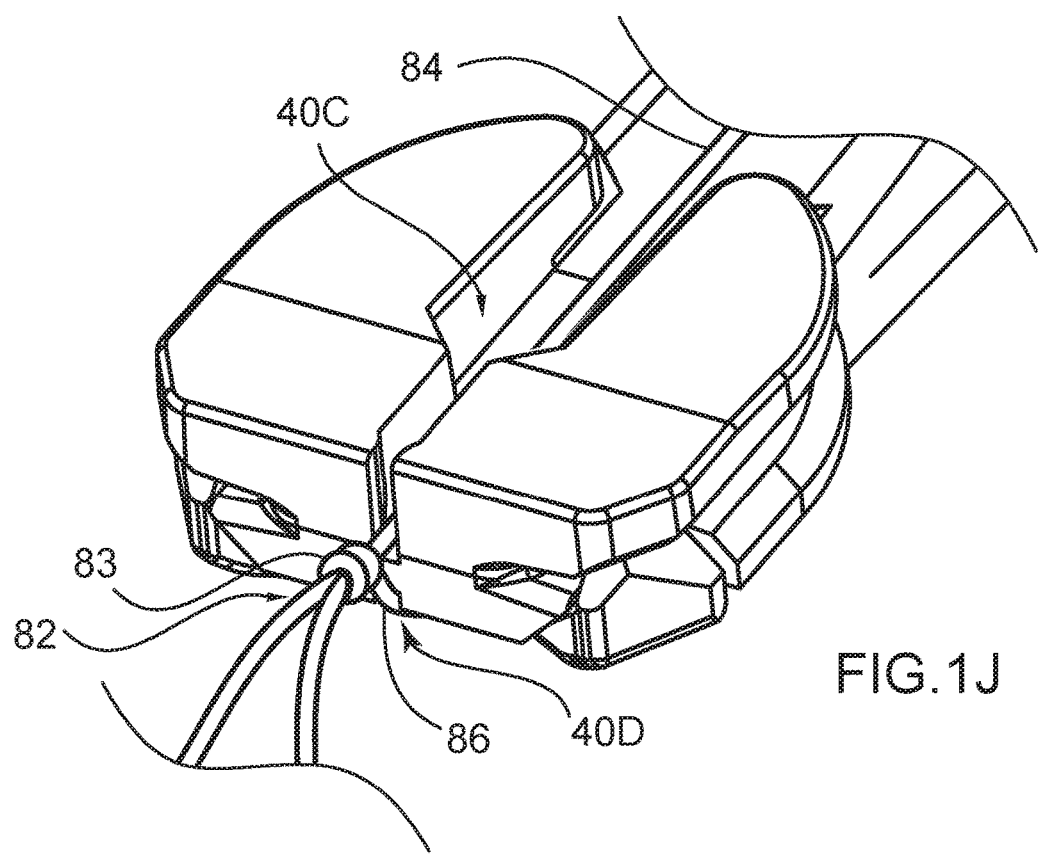
FIG. 1J illustrates a top front perspective view of a distal portion of a knot pusher in accordance with an alternate embodiment of the present invention.

In an additional embodiment of the present invention, the distal head 30 may comprise an additional suture receiving element associated with the bottom wall, i.e. a bottom wall suture receiving element. The bottom wall suture receiving element may be a groove, specifically an opposing groove 40D that is or is not aligned with the intermediate groove 40 but is formed within the bottom wall 34. The opposing groove 40D, as shown in FIG. 1I and FIG. 1J, extends proximally from the knot pushing surface 38 and extends longitudinally along the bottom wall 34 opening into exterior surface of the bottom wall 34. In some embodiments, the opposing groove 40D may be formed within the support 31' such as the central support 31 described above along the bottom wall or face 32. The opposing groove 40D facilitates locking of a sliding knot such as a Dines knot during use by allowing the sliding knot to be held in position against the distal knot pushing surface 38. In other words, the distal head comprises an opposing groove that in one embodiment is aligned with the intermediate groove and formed within the bottom wall, to facilitate tightening of the sliding knot prior to locking of the sliding knot in its tightened configuration. The method of use of a knot pusher 100A with a distal head 30 having an additional opposing groove 40D, is described further herein below with respect to FIGS. 7A-7B and FIG. 1I and FIG. 1J.

Figure 1K:
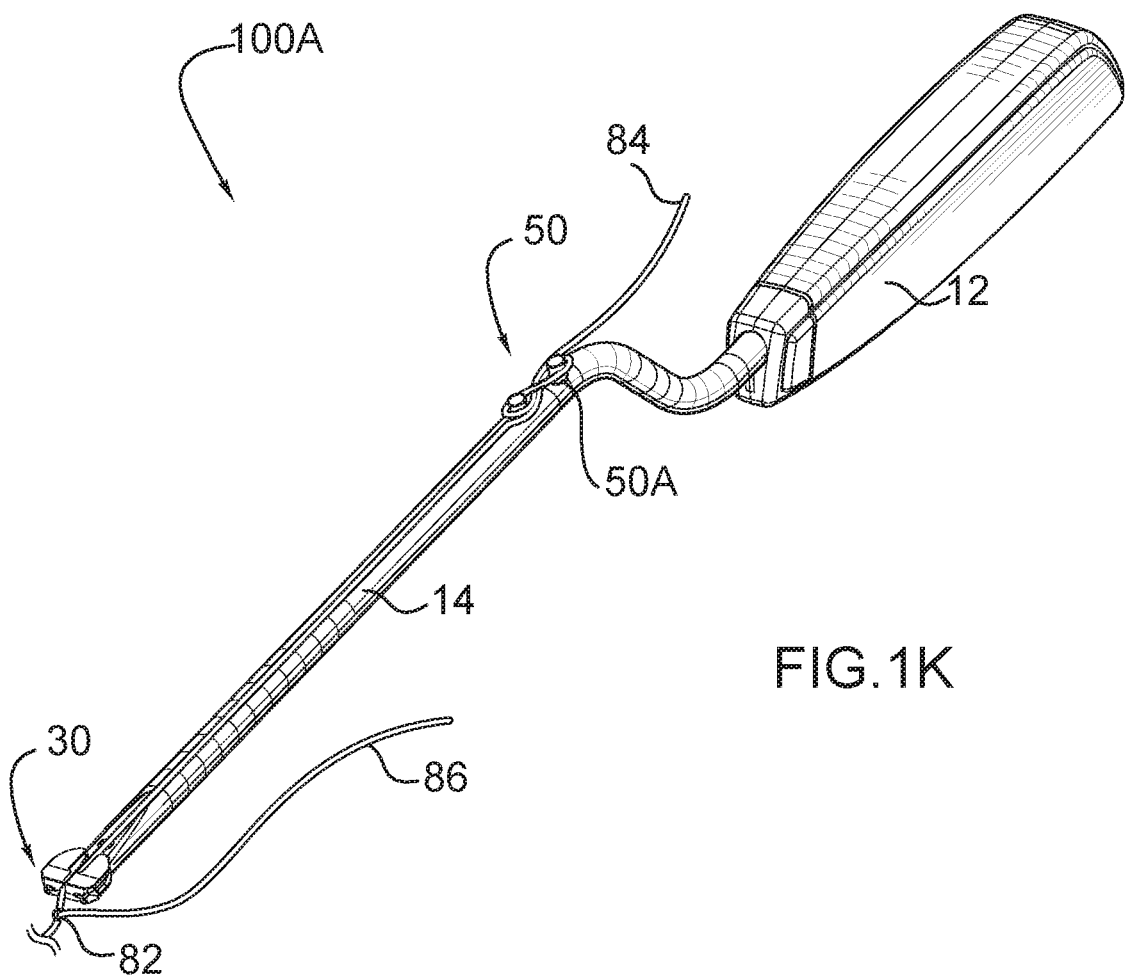
FIG. 1K illustrates a top front perspective view of a knot pusher comprising a tensioning aid in accordance with an embodiment of the present invention.
Figure 1L:
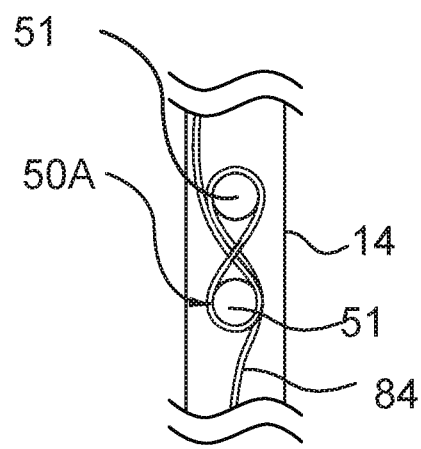
FIGS. 1L-1N, each illustrate top views of a tensioning aid of a knot pusher in accordance with alternate embodiments of the present invention.

In an additional embodiment, as shown in FIG. 1K, the knot pusher 100A additionally comprises a tensioning aid or tension maintaining element 50 that is positioned, for example, along a front or top face of the shaft 14 of the knot pusher 100A. The tensioning aid 50 functions to keep tension on the strand of suture that is held within the intermediate groove 40C (such as within the central groove 40C'). In one specific example, as shown in FIG. 1L, the tensioning aid 50 defines a double-peg configuration 50A, that comprises two pegs 51 that are mounted on the front or top face of the shaft 14. The two pegs 51 allow the strand of suture (which may comprise a post 84, as described later herein), to be wrapped around them. More specifically the strand of suture is routed through the two pegs 51 in a figure eight configuration thereby securing the suture to the shaft 14 of the knot pusher 100A. In other embodiments, the tensioning aid 50 may comprise a configuration having one or more pegs. The method of use of the tensioning aid 50 is described further herein below with reference FIGS. 7A-7E that illustrate the steps of a method of using the knot pusher 100A.

Figure 1M:
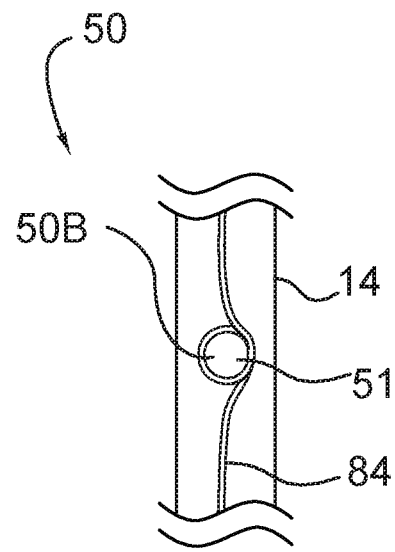
Figure 1N:
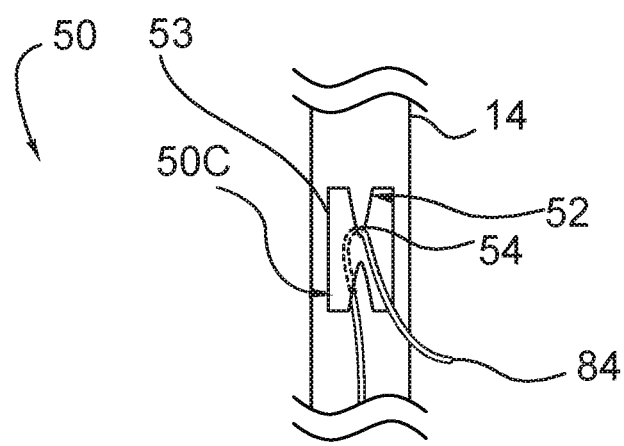

In an alternate configuration as shown in FIG. 1M, the tensioning aid 50 comprises a single-peg configuration 50B. The post 84 may be wound around the peg 51 to be secured to the shaft 14. In a still further alternative, as shown in FIG. 1N, the tensioning aid 50 comprises a catch or clip 50c that comprises a main body 53 that is mounted on the shaft 14. For example, the main body 53 may be coupled to the shaft 14 via a protrusion. The main body 53 is spaced apart from the shaft 14 such that a gap is present between the main body and the shaft 14, to allow the post 84 to be routed through the gap. The main body further comprises at least one slit or opening 52 formed therein that defines two arms 53a and 53b for retaining the one of the two strands of suture there-between to secure said one of the two strands of suture to the shaft. In some examples, the opening 52 narrows at its base in the proximal direction forming an apex 54 which functions to pinch the strand of suture after it is passed behind the main body 53 and then through the opening 52 such that it passes in front of the main body 53 thereafter allowing the post 84 to be pinched at the apex 54.

Figure 4A:
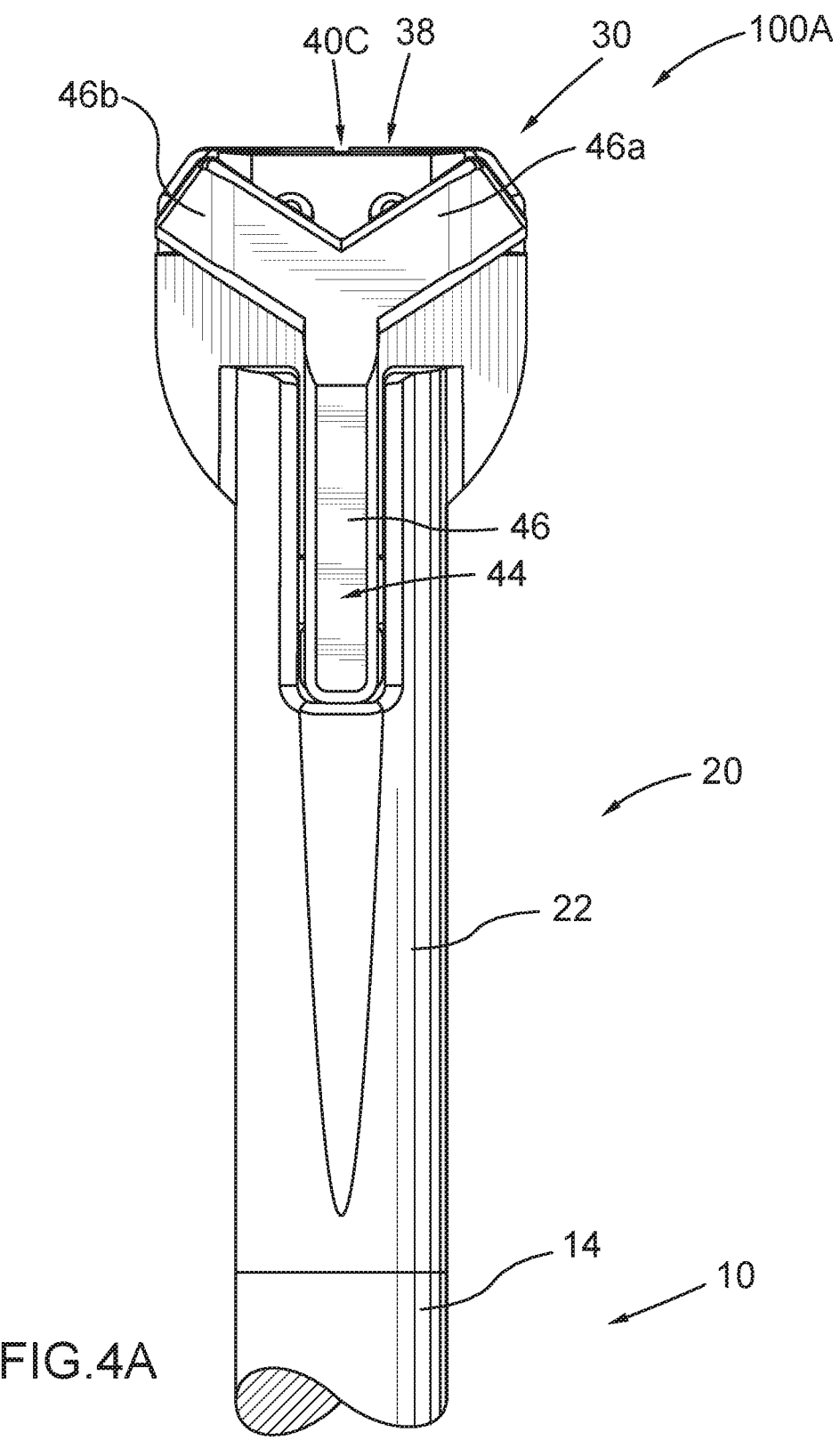
FIG. 4A illustrates a bottom view of a distal portion of a knot pusher in accordance with an embodiment of the present invention.
Figure 4B:
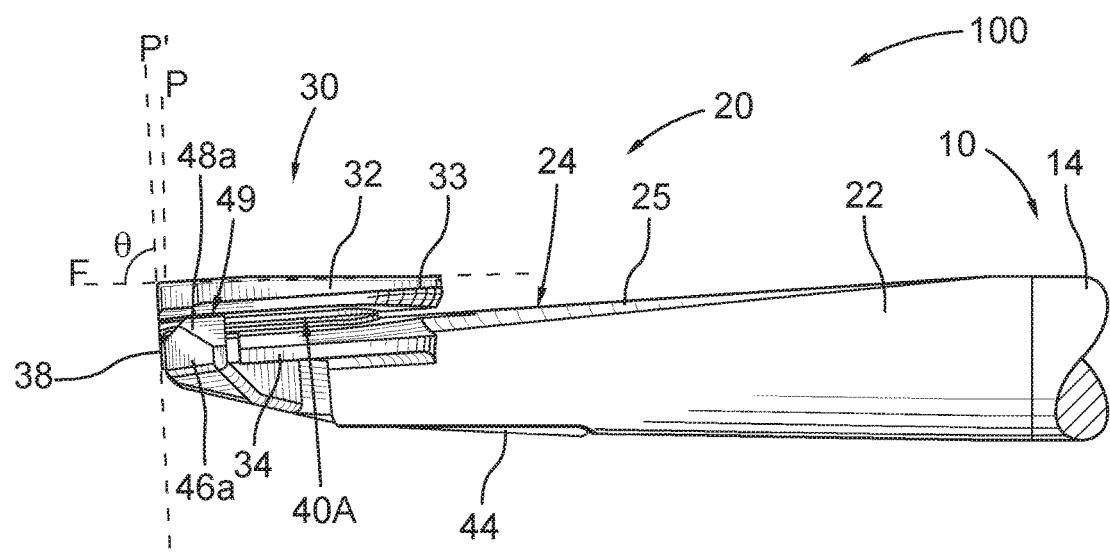
FIG. 4B illustrates a right side view of a distal portion of a knot pusher in accordance with an embodiment of the present invention.
Figure 4C:
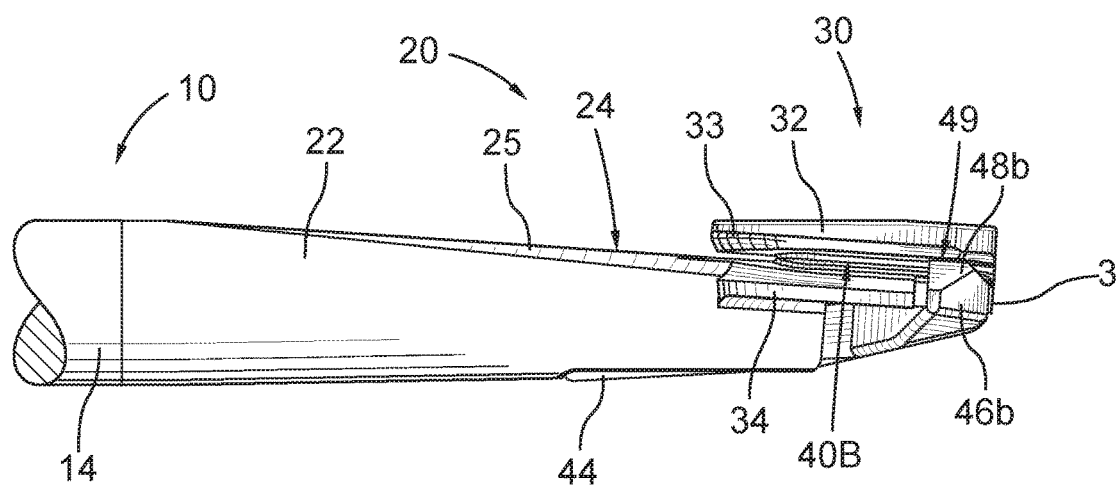
FIG. 4C illustrates a left side view of a distal portion of a knot pusher in accordance with an embodiment of the present invention.
Figure 4D:
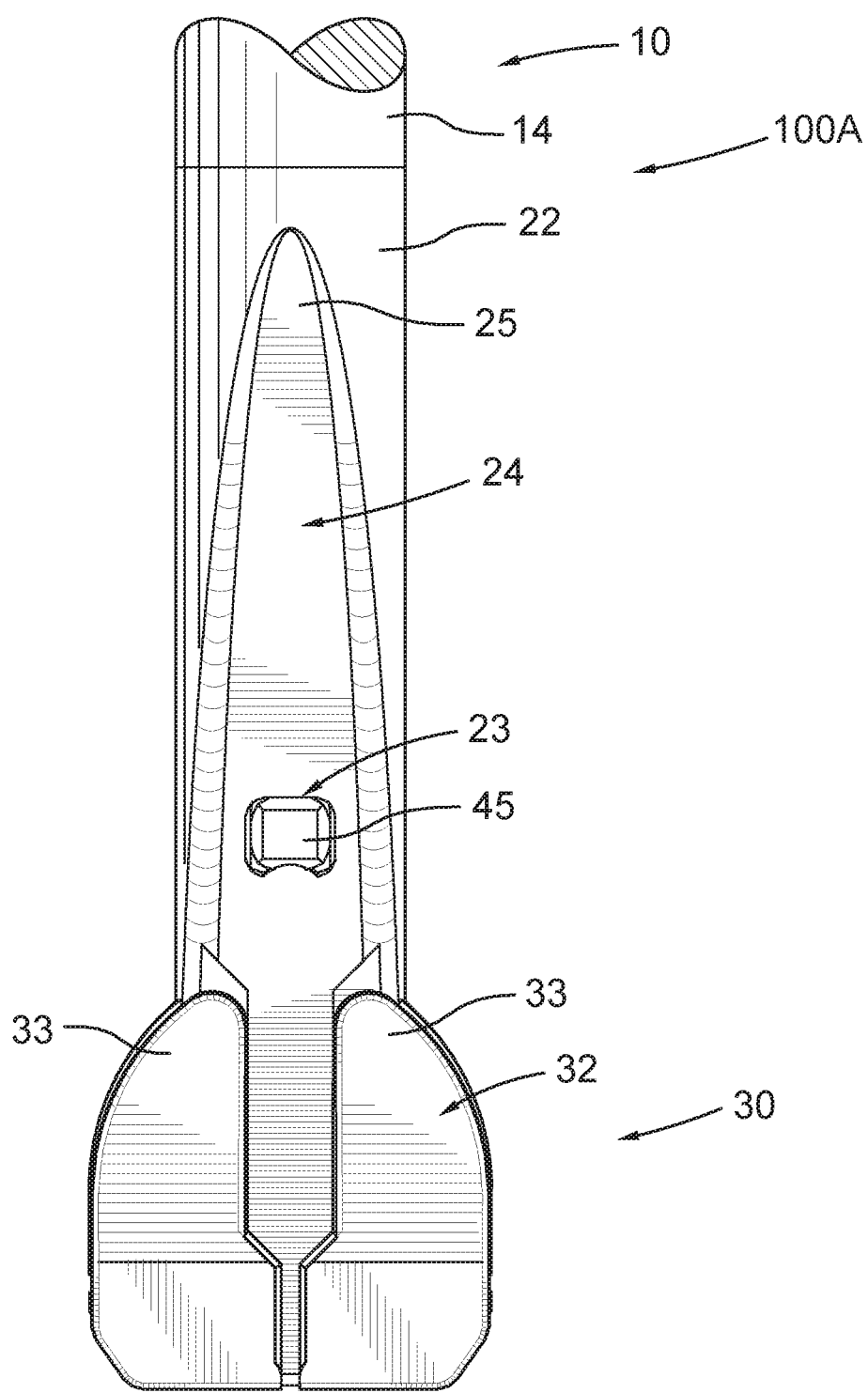
FIG. 4D illustrates a top view of a distal portion of a knot pusher in accordance with an embodiment of the present invention.

In some embodiments, as shown in FIGS. 4A, 4B, and 4C, the distal head 30 may additionally comprise a side groove suture retention feature such as a side groove suture retaining element that is associated with one or more of the side grooves 40A, 40B. In some embodiments, the suture retention feature for the side grooves 40A, 40B may be similar to the suture retention feature described herein previously with respect to the intermediate groove 40C. In one particular example, the side groove suture retaining element comprises a snap arm 44 that is coupled to the neck 22, for example via a force fit or snap fit arrangement. The snap arm 44 comprises snaps 46a and 46b that extend radially from a longitudinally extending stem 46. In one specific example, further shown in FIG. 1B and FIG. 2, a tab 45 of the snap arm is received within an opening 23 within the neck 22 and engages therewith. In the illustrated embodiment, the snaps 46a and 46b each form a portion of bottom wall 34. In some embodiments, the snap arm 44 is resilient allowing the snaps 46a and 46b to flex from their nominal or closed position to an open position to allow the two ends of the suture to be received within the opposed side grooves 40A and 40B. Thereafter the snaps 46a and 46b return to their nominal or closed position to retain the two suture ends in each of said side grooves 40A and 40B.

In one specific example, as shown in FIGS. 4B and 4C, each of the snaps 46a and 46b comprise a projection 48a, 48b respectively that projects away from the bottom wall 34 towards the top wall 32, such that there is a minimal clearance or gap 49 between the walls, substantially preventing the suture from exiting the side grooves 40A, 40B. In some embodiments, when the snaps 46a, 46b are in the closed position, the clearance or gap 49 is smaller than the outer diameter or width of the suture to retain/constrain the suture within the side grooves 40A, 40B and prevent the suture from passing through the gap 49 during the process of pushing the knot. Additionally, the snaps reduce the risk of the suture strands falling out of position from within the side grooves 40A and 40B when tension is not maintained on the suture strands. This helps to minimize the risk of suture strands exiting the side grooves 40A, 40B during the procedure and thus helps to minimize the need to reinsert the suture strands within the side grooves 40A and 40B as the knot pusher is being advanced distally to push the knot. In some embodiments, the pair of snaps 46a and 46b comprise hinged snaps that act to constrain or lock the strands of suture within the side grooves 40A, 40B. The side grooves 40A, 40B are of a sufficient depth to retain the suture. In some embodiments, the snaps 46a and 46b are chamfered to facilitate the loading of the suture within the side grooves 40A, 40B.

In some embodiments, the neck 22 comprises a tapered portion 24 along a top face thereof that leads into the opposed side grooves 40A and 40B, as shown in FIGS. 4B and 4C. The neck 22 tapers into the opposed side grooves 40A and 40B such that the top face of the neck 22 is flush with the inner surface of the bottom wall 34. As each of the opposed side grooves 40A and 40B are formed contiguously with the tapered portion 24, it allows the two strands of suture to be guided/lead into the side grooves 40A, 40B. In other words, the tapered portion 24 is continuous with the side grooves 40A and 40B. This may allow for easier loading of the suture strands within the knot pusher 100A to facilitate the knot pushing procedure. In some embodiments, the tapered portion 24 comprises a flat planar surface 25.

In some embodiments, each of the side grooves 40A and 40B defines a curve, or alternatively, extends radially away from a central axis of the distal head 30. The curved side grooves 40A and 40B extend proximally from the distal knot pushing surface 38 towards the neck 22. In some embodiments, a part of the top wall 32 that extends proximally from the central support 31, forms overhangs 33, as shown in FIG. 4B. A portion of each of the side grooves 40A, 40B is formed between an overhang 33 and the neck 22. The overhangs 33 function as hooks to facilitate capturing of the suture by the distal head 30. Using the hooks, the two strands of suture may easily be guided into the side grooves 40A, 40B to allow for easier loading of the suture into the knot pusher 100A.

With reference now to FIG. 4B, in some embodiments the knot pusher 100A may comprise additional features to facilitate loading of the suture and/or pushing of the knot. In some such embodiments (not illustrated), the knot pushing surface 38 may be defined (or may extend) along a plane P that is perpendicular to the longitudinal axis (along plane F) of the knot pusher. In other embodiments (as illustrated), the knot pushing surface 38 defines a taper such that the knot pushing surface 38 is at an incline relative to plane P. In some embodiments, a plane P' of the knot pushing surface 38 is at an angle θ (with respect to the top face 32 defined by plane F) which is less than about 90 degrees (or, put differently, the plane P' is oriented at an angle [180−θ] that is greater than about 90 degrees from the longitudinal axis of the knot pusher 100). In a specific example, the angle θ between the knot pushing surface 38 and the top face 32 is about 89 degrees. The incline of the knot pushing surface 38 helps to retain the knot away from the opening of the intermediate groove 40C (see FIG. 2). The distal knot pushing surface 38 of the knot pusher is angled away from the perpendicular such that as the knot is pushed and tightened, a component of the longitudinally directed force acts to direct the knot (down and) away from the opening of the intermediate groove 40C. The inclined knot pushing surface 38 may help prevent a knot such as a sliding knot from disengaging from the knot pusher 100A to prevent patient injury or to avoid the requirement of re-engagement of the knot with the knot pusher 100A.

As shown in FIG. 1A, the knot pusher may have a length 1. In some embodiments, length 1 may be equal to between about 3.00" (inches) to about 20.00". In one specific example, the knot pusher 100A has a length 1 that is equal to about 11.09". As noted previously, the knot pusher 100A comprises a distal portion 20 that is coupled to the shaft 14 of the proximal portion 10. As shown in FIG. 1D, the distal portion 20 may have a length Y. In some embodiments, length Y of the distal portion 20 may be equal to greater than about 0.10". In one such example, the distal portion 20 may form a significant portion or majority of the device that extends distally beyond the handle 12. As illustrated in FIG. 1D, in one specific example, the distal portion 20 has a length Y equal to about 1.00". Furthermore, the shaft 14 and the distal portion 20 may have a combined length S of about 2.00" to about 19.00", for example about 7.35". Additionally, the shaft 14 may have a width $S_w$ of between about 0.10" to about 1.00" and more specifically, from about 0.10" to about 0.50". In one specific example, the shaft 14 has a width, $S_w$, of about 0.20".

As discussed previously, the shaft 14 is coupled to the distal portion 20; the distal portion 20 further comprising a distal head 30. As shown in FIG. 1E, the width of the distal head is defined by U. In some embodiments, the distal head 30 may have a width U of between about 0.10" to about 1.00" and more specifically, from between about 0.10" to about 0.50". In one specific example, the distal head 30 has a width U equal to about 0.33".

In some embodiments, the length of the side grooves 40A, 40B may be substantially equal to the length of the top and bottom walls 32, 34. In one specific example, as shown in FIG. 1D, the top and bottom walls 32, 34 have lengths Z, W that are equal to about 0.33" and 0.32", respectively. Furthermore, the two opposed side grooves extend from the distal knot pushing surface 38 by a length that is equal to about 0.33". In some embodiments, the length of the distal head 30 and each of the side grooves 40A and 40B may range from between about 0.10" to about 1.00", and more specifically, from between about 0.10" to about 0.50". In other embodiments, the length of the distal head 30 may be greater than about 1.00".

As noted previously, the distance between the side grooves 40A and 40B may be defined by the width of the central support 31. In some specific embodiments, the distance between the side grooves may be equal to or greater than about three times the width/diameter (these terms being used interchangeably herein) of the suture to be used. In one specific example, the spacing between the side grooves 40A, 40B, and thus the width of the central support 31 is about 0.012" where the width of the suture to be used is about 0.004". Thus, the spacing between the side grooves may correspond (i.e. be proportional) to the size of the suture being used. In some embodiments, the spacing between the side grooves may correspond to a suture of up to a size 5; that is, in these embodiments, the spacing between the side grooves may be up to about three times the width of a 'size 5' suture, depending on the suture intended to be used with the device. In other embodiments, the side grooves 40A, 40B may be spaced apart by a distance of between about 5 times the width of the suture to about 70 times the width of the suture. In one specific embodiment, the side grooves 40A and 40B are spaced apart by a distance of about 10 times the width of the suture being used. In one such device as shown in FIG. 1E, which may be used, for example, with a 2-0 suture, the width X of the central support 31 and thus the distance between the side grooves 40A, 40B, is equal to about 0.11" which is equal to about 10 times the width of a 2-0 suture.

In some embodiments, the distance between the side grooves 40A, 40B may correlate with the actual width of each of the side grooves 40A, 40B, rather than being proportional to the width of the suture to be used. With reference again to FIG. 1E, the distance between the side grooves 40A, 40B (i.e. the width X of central support 31) is approximately equivalent to the width U of the distal head 30 subtracted by the widths of the side grooves 40A, 40B. In a particular example of this, the width of the central support 31 is about 0.11" which is equal to the width of each of the two side grooves 40A and 40B. In some embodiments, the distance between the side grooves may correspond to between about 5 times to about 70 times the width of the side grooves 40A, 40B. In some such embodiments, the width of each of the side grooves is equal to the width of suture to be used.

Referring now to FIG. 1D, the central support 31 of the distal head 30 defines a length V that is less than the total length W of the distal head 30, allowing an overhang 33 to be formed as a result. More specifically, the proximal portion of each of the side grooves 40A and 40B may be defined by overhangs 33 formed by proximal portions of the top wall 32 that extend proximally from the central support 31. The overhangs may have a length that is roughly equal to the length W of the distal head 30 subtracting the length V of the support 31. In one specific example, the central support 31 has a length V of about 0.250" and the overhangs 33 each have a corresponding length of about 0.076", i.e. the proximal portion of each of the side grooves 40A and 40B has a length of about 0.076".

Referring again to FIG. 2, at least a portion of the intermediate groove 40C, such as the distal portion 40Cd, may have a width that is substantially equal to the width of the suture being used. More specifically, the distal portion 40Cd of the intermediate groove 40C is dimensioned such that it is sufficiently wide so as to allow a suture to be positioned there-through. In some embodiments the distal portion 40Cd may have a width that is between about 1 times the suture width to about 3 times the suture width. Limiting the width of the intermediate groove may aid in preventing a knot positioned at the distal knot pushing surface 38 from being pulled into the intermediate groove 40C. In some embodiments, the width of the intermediate groove distal portion 40Cd may range from about 0.012" to about 0.042". In one specific example, as shown in FIG. 1E, the distal portion of the intermediate groove 40C has a width X' of about 0.025" for use with a suture of 0.011" width. In another example, for use with a suture having a suture width of about 0.004", the intermediate groove distal portion 40Cd has a width of about 0.012".

In some embodiments, the width of proximal portion 40Cp of the intermediate groove 40C is substantially equivalent to the width of distal portion 40Cd. In alternate embodiments, the width of central groove 40C along proximal portion 40Cp is greater than the width along distal portion 40Cd. In some such embodiments, the width of proximal portion 40Cp is slightly less than the total distance between the side grooves 40A, 40B.

In some embodiments, as illustrated for example in FIG. 1A, the distal head 30 of the knot pusher may be offset from the handle 12, to enhance visualization and line of sight for the distal head 30 during the procedure. In other words, the longitudinal axis of the distal head differs from/is offset from the longitudinal axis of the handle, i.e. the distal head may be misaligned or planarly offset (although the respective planes defined by the handle and distal head may be parallel to one another, as shown) relative to the handle. This helps to prevent the physician's hand from blocking the distal head 30 from view. In some embodiments, the distal head 30 may be offset from the handle 12 by between about 1.0" to about 4.0". In a specific example of an embodiment where the distal portion 20 is transversally offset from the handle 12, the top surface of the top wall 32 is offset from a bottom surface of the handle 12 by about 1.74". In still other embodiments, the handle 12 may not be offset from the distal head 30 and may be coaxially aligned with the distal head 30.

In some embodiments, the handle 12 may have a width ranging from about 0.5" to about 1.0" and a length of about 1.0" to about 5.0". In one specific example, the handle 12 has a width hw of about 0.56" and a length of about 3.74". In another example, the handle 12 may be sized, configured and shaped to define an ergonomic pen-like grip. Thus, in accordance with some embodiments of the present invention, the handle has an ergonomic shape that allows the handle to be held comfortably and easily. In some embodiments, portions of handle 12 may be coated/covered/overlaid with a material suitable for gripping/grasping and manipulating the knot pusher. For example, handle 12 may include ergonomic side grips on one or more sides of the handle, the side grips comprising a thermoplastic elastomer such as Santoprene®. In alternative embodiments, other materials may be used. The aforementioned dimensions have been found to be particularly well-suited for a knot pusher used for the closure of defects in the annulus fibrosus of an intervertebral disc, as well as for other similar applications.

Figure 5B:
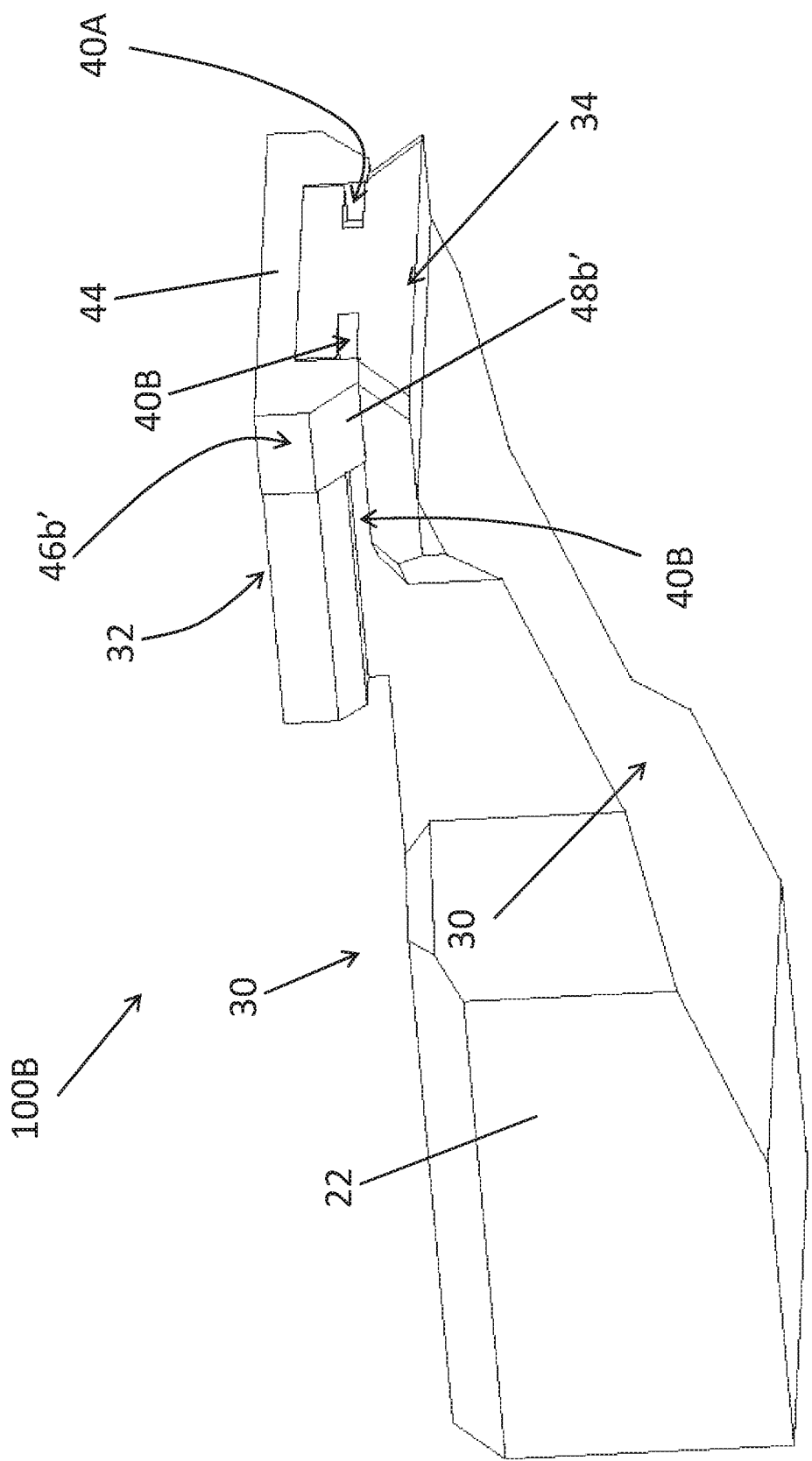

In an alternative embodiment, as shown in FIGS. 5A-5B, a knot pusher 100B comprises a snap arm 44' that may be coupled to a top surface of the shaft 14 or neck 22. The snaps 46a' and 46b' form a portion of the top face 32 of the knot pusher 100B. The snaps 46a', 46b' function in a similar manner to snaps 46a and 46b to retain the suture within side grooves 40A and 40B to prevent the suture from disengaging from the distal head 30 of the knot pusher when tension is released. The snaps 46a' and 46b' comprise downwardly extending projections 48a', 48b' that extend towards the opposing wall which in this example comprises the bottom wall 34 so that the suture is retained there-between. The embodiment shown in FIGS. 5A-5B may additionally comprise an intermediate groove 40C (not shown) for allowing advancement of a sliding knot.

Figure 6A:
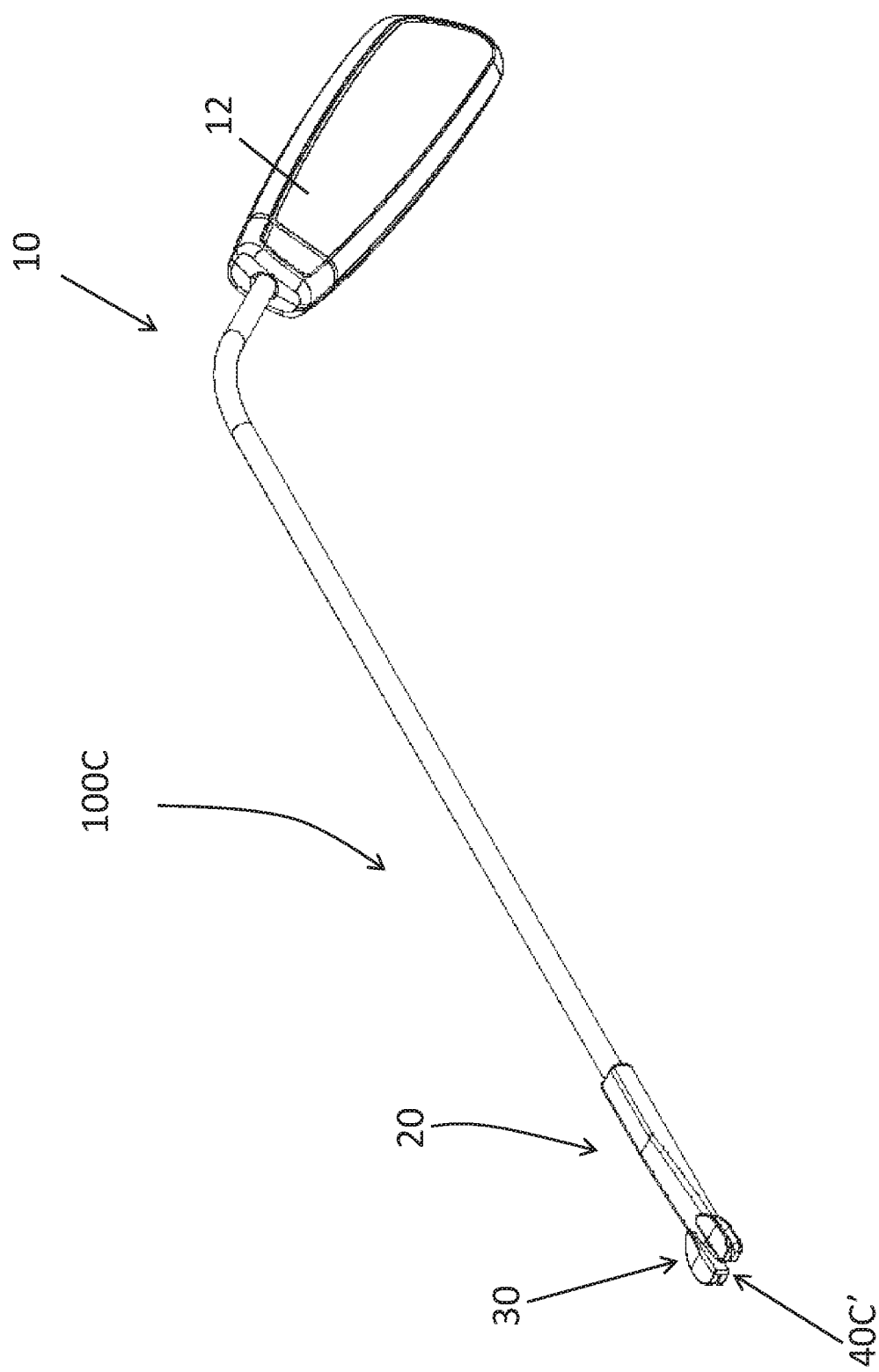
Figure 6C:
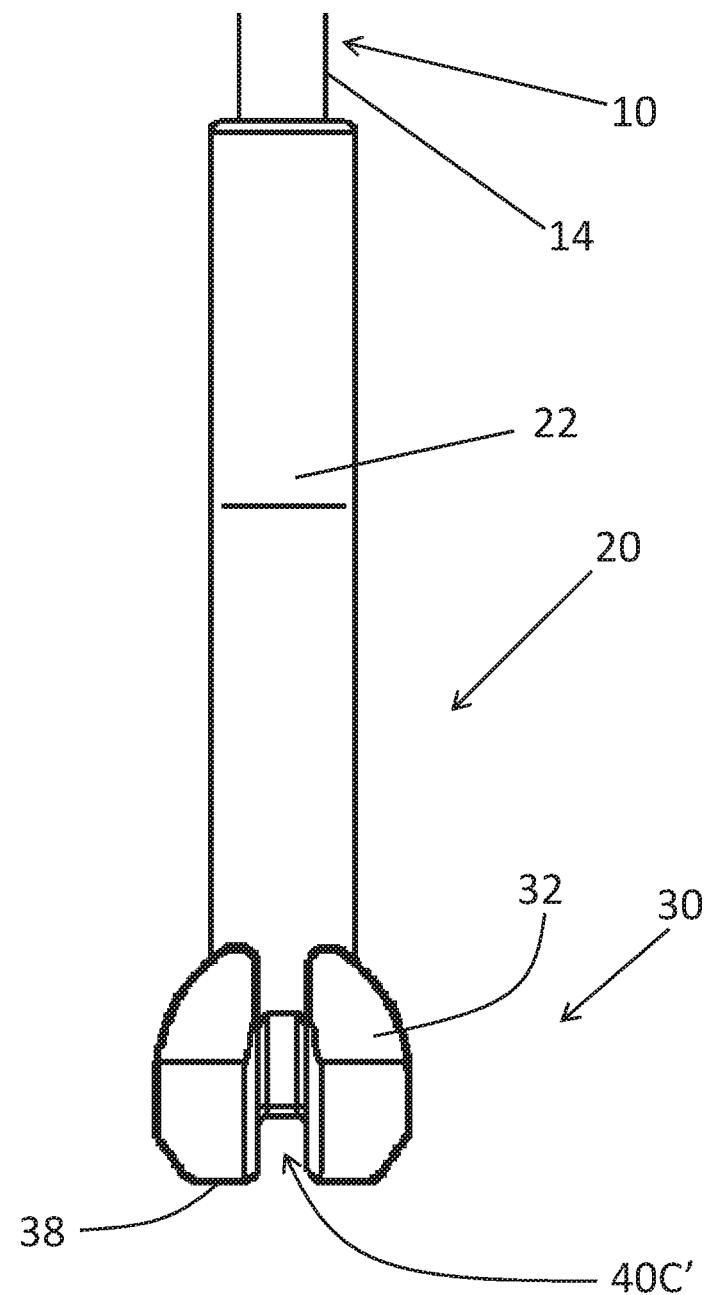

In a further alternative embodiment, as shown in FIGS. 6A-6C, a knot pusher is disclosed having a central viewing channel. The knot pusher 100C comprises a proximal portion 10 comprising a handle 12 and a shaft 14. The knot pusher 100C further comprises a distal portion 20 comprising a neck 22 and a distal head 30 with the distal head defining side grooves 40A and 40B between top and bottom walls 32, 34 (34 not shown in Figures but is on the bottom/underside surface of knot pusher 100C). The distal head defines a central channel or groove 40C' that extends longitudinally through the top face 32 of distal head 30. The intermediate groove or channel 40C' extending from the proximal part of the distal head 30 through to the knot pushing surface 38. The intermediate groove 40C' acts a viewing channel to permit viewing of the overhand knot to facilitate tightening of the overhand knot.

With reference to FIG. 6A, an alternative embodiment of an offset shaft is illustrated. In this particular embodiment, the shaft is curved so as to define a non-parallel longitudinal axis relative to the handle 12.

As discussed previously, in some medical applications it is desirable to apply one or more knots in order to approximate tissue and to secure the suture that has been passed through a region of tissue. For example, one or more knots may be applied to suture that has been passed through a region of tissue having a defect in order to: (a) aid in approximating the tissue; and (b) secure the suture around the defect. Some such applications require the use of both sliding and overhand knots, which knots have differing mechanisms for advancing to the tissue site as well as for tightening at the tissue site. In applications where the tissue site being treated is remote or where the access to the tissue site is limited for any other reason, it may be desirable to use a knot pusher to advance and/or tighten the knot(s). Thus, in such applications where access to the tissue being sutured is restricted and where both types of knots are desired/required to complete the procedure, it would be beneficial for the user to be able to utilize the same device for advancing and tightening both forms of knots.

In some such applications, a sliding knot is advanced to the tissue site in order to treat the defect within the region of tissue while one more half-hitches or other types of overhand knots may be subsequently applied in order to secure the sliding knot in place. These additional knots help to ensure that the sliding knot does not open or unravel following the procedure.

In accordance with an embodiment of such a procedure, a method of using a knot pusher such as described herein above is disclosed for advancing/pushing both a sliding knot and an overhand knot during the course of the procedure. In one particular example of this embodiment, the tissue site may comprise a region of tissue defining a defect, for example within an annulus fibrosis of an intervertebral disc. In one such example, access to the intervertebral disc may be provided through a surgical portal, inserted for example through a lamina of a vertebra, to allow the suture to be passed through the affected disc tissue.

Following passage of a suture loop around the defect, for example as disclosed in U.S. provisional patent application Ser. No. 61/597,449, filed on Feb. 10, 2012 and incorporated herein by reference in its entirety, a sliding knot may be deployed to secure the suture. The knot pusher is used to advance the sliding knot along the suture through the portal to enable approximation of the tissue at the defect and further to tighten and lock the sliding knot. In order to secure the sliding knot at the surface of the disc, one or more additional half-hitches or other overhand knots are applied over the sliding knot.

Figure 7A:
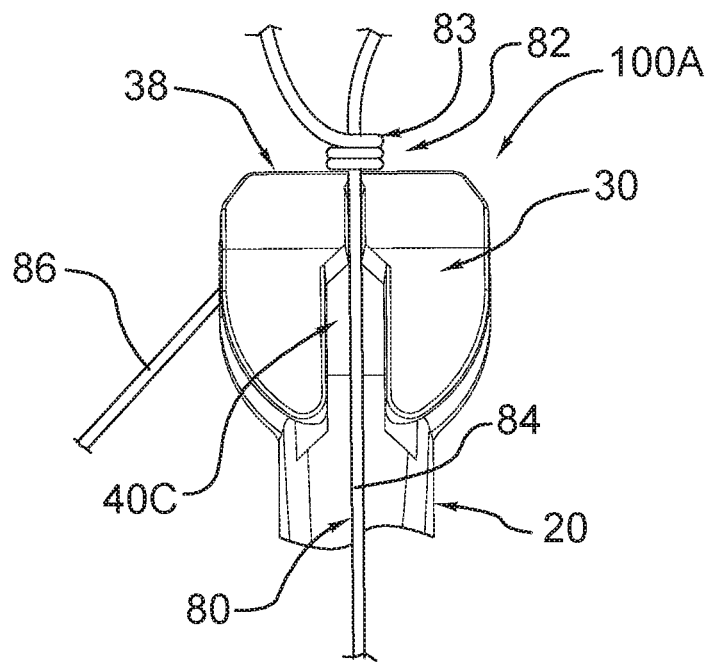
FIGS. 7A-7E illustrate a method of using a knot pusher in accordance with an embodiment of the present invention.
Figure 7B:
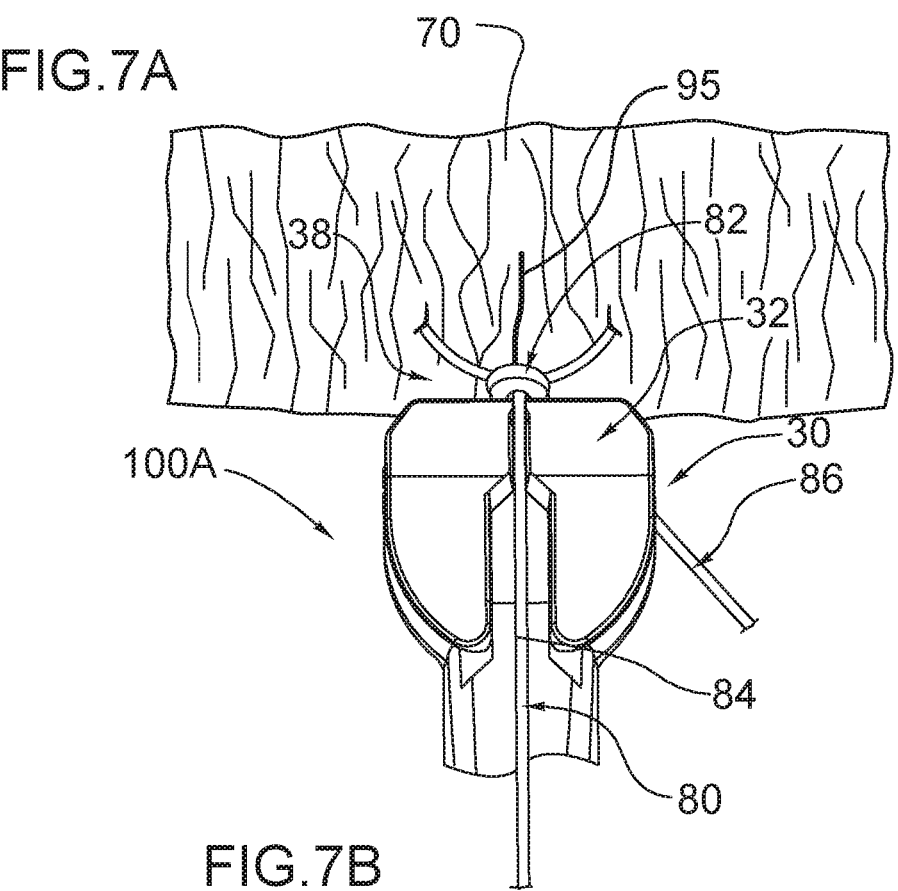

The sliding knot may be formed after the suture has been passed through the disc or may be a pre-formed or pre-tied knot that is deployed thereafter. As shown in FIGS. 7A-7B, the sliding knot 82 terminates in two strands of suture with one strand being defined as a post 84 and the second strand of suture being defined as a locker 86, which terms are known to those of skill in the art.

The following discussion references FIGS. 7A-7E. In one specific example of a method of the present invention, the sliding knot 82 comprises a Dines knot 83. As shown in FIG. 7A, the post 84 is placed within the intermediate groove 40C—specifically the central groove 40C' with the sliding knot 82 resting against the distal knot pushing surface 38. The knot pusher or device 100A is then advanced towards the tissue site, for example through a portal allowing the distal head 30 to push or advance the sliding knot 82 by pushing directly on the sliding knot 82. Tension is maintained on post 84 as the knot pusher 100A is advanced. A longitudinally directed force is applied against the sliding knot 82 by the distal knot pushing surface 38, such that it slides along the post 84 distally (for example through the portal) until it is positioned at the tissue surface 70 having a defect 95 as shown in FIG. 7B, where the tissue may be, for example, an annulus fibrosis of an intervertebral disc. A proximal 'pulling' force is applied to the post 84 to maintain it in tension as the sliding knot 82 is advanced in order to approximate the tissue.

Furthermore, in embodiments where the knot pushing surface 38 is inclined—for example, as shown in FIG. 4b—the incline allows a component of the longitudinally directed force to direct the sliding knot 82 away from the opening of the central groove 40C'. This enables the sliding knot 82 to remain engaged with the knot pushing surface 38 as the knot pusher 100A is advanced to further aid in tightening the sliding knot 82.

In one specific embodiment, where the sliding knot 82 is a Dines knot 83, continuous tension is applied using the knot pusher 100A to approximate the defect. In other embodiments, the knot pusher 100A may be pushed against the sliding knot 82 at the tissue surface and released. This may be repeated (i.e. the act of pushing and retracting) a plurality of times in order to further tighten the sliding knot 82. In such an embodiment, the knot pusher 100A may be pushed and released four times until the sliding knot is fully cinched. At this step, a determination is made as to whether tissue approximation at the defect 95 is adequate. If the tissue approximation is not deemed to be sufficient, the step of pushing and releasing the knot pusher 100A may be repeated further.

Once the tissue has been approximated to the extent desired, tension is maintained along the post 84 whilst the locker 86 is pulled to lock that position of the Dines knot, i.e. the locker 86 is pulled until the sliding knot 82—which in this particular case comprises the Dines knot 83—reconfigures. This locks the Dines knot 83. In some embodiments, the locker 86 may be pulled and released more than once in order to ensure complete locking of the Dines knot 83. In one specific example, the locker 86 may be pulled and released four times. The knot pusher 100A may then be withdrawn through the portal.

In one particular example, as shown in FIG. 1J, the distal head 30 comprises an intermediate groove 40C as well as an opposing groove 40D. In one such embodiment the intermediate groove comprises a central groove 40C'. In accordance with a method of the present invention, the post 84 of the suture is placed or received within the central groove 40C and pulled to hold the sliding knot 82 such as the Dines knot 83 in place against the distal knot pushing surface 38, similar to the discussion above with reference to FIGS. 7A and 7B. The locker is then pulled underneath the distal head 30 along the bottom wall 34 to be placed or received within the opposing groove 40 and held therein. When the post 84 and the locker 86 are held in this orientation, it allows the post 84 to be pulled with sufficient force to optimize the tension placed on the Dines knot 83. This allows the Dines knot to be tightened sufficiently to ensure effective approximation of the tissue. The post 84 is kept taut and in tension such that force is maintained against the Dines knot 83 until the locker is pulled, thus locking the Dines knot 83 in its tightened configuration. Therefore, the opposing groove 40D allows the sliding knot 82 to be held in position against the distal knot pushing surface 38 to optimize tightening and locking of a 'sliding and locking knot' such as the Dines knot 83.

In some embodiments, to facilitate tightening and locking of the sliding knot 82 such as the Dines knot 83, the knot pusher 100A may additionally comprises a tensioning aid 50 as discussed previously and shown in FIGS. 1K-1N. The tensioning aid 50 maintains tension on the post 84 during use. After the knot pusher 100A has been advanced into the tissue at the target site to position a sliding knot 82 therein. The post 84 is pulled to tighten the Dines knot 83 to ensure that the tissue has been approximated to the desired extent before the Dines knot 83 can be locked. The post 84 can then be held by the tensioning aid 50. For instance, the post 84 can be wrapped around the tensioning aid 50 or caught within a slot of the tensioning aid 50 to be held by it. For example as shown in FIG. 1K, the post 84 is wrapped around the double post configuration 50A in a figure eight. As such, the tensioning aid 50 functions to maintain tension on the post 84 after the post 84 has been pulled to tighten the sliding knot 82, and thereby allows the operator to partially or fully release the post 84. Releasing the post 84 allows the operator to hold the handle of the knot pusher 100A with one hand and the locker 86 to be pulled with the other free hand once the sliding knot 82 is at it its desired tightness. Thus the locker 86 can be pulled simultaneously as the post 84 is pulled. Furthermore, the tensioning aid 50 allows the physician for example that is using the knot pusher 100A to free up one hand to allow the physician to use other instruments during the procedure.

In summary, some embodiments of a method of the present invention provide for a method comprising the steps of: applying tension to one of the two strands of suture such as the post 84 to tighten said sliding knot 82 to a desired extent into a tightened configuration to approximate the tissue at the defect. This may be facilitated, for example, by providing an opposing groove 40D as mentioned above. Tension may then be maintained on the post 84 to maintain said sliding knot 82 in its tightened configuration. This may be facilitated, for example, by providing a tensioning aid 50 to secure the strand of suture such as the post 84 to the shaft 14 of the knot pusher 100A. Tension can then be applied simultaneously to the other of the two strands of suture to lock the sliding knot 82 in its tightened configuration.

Figure 7C:
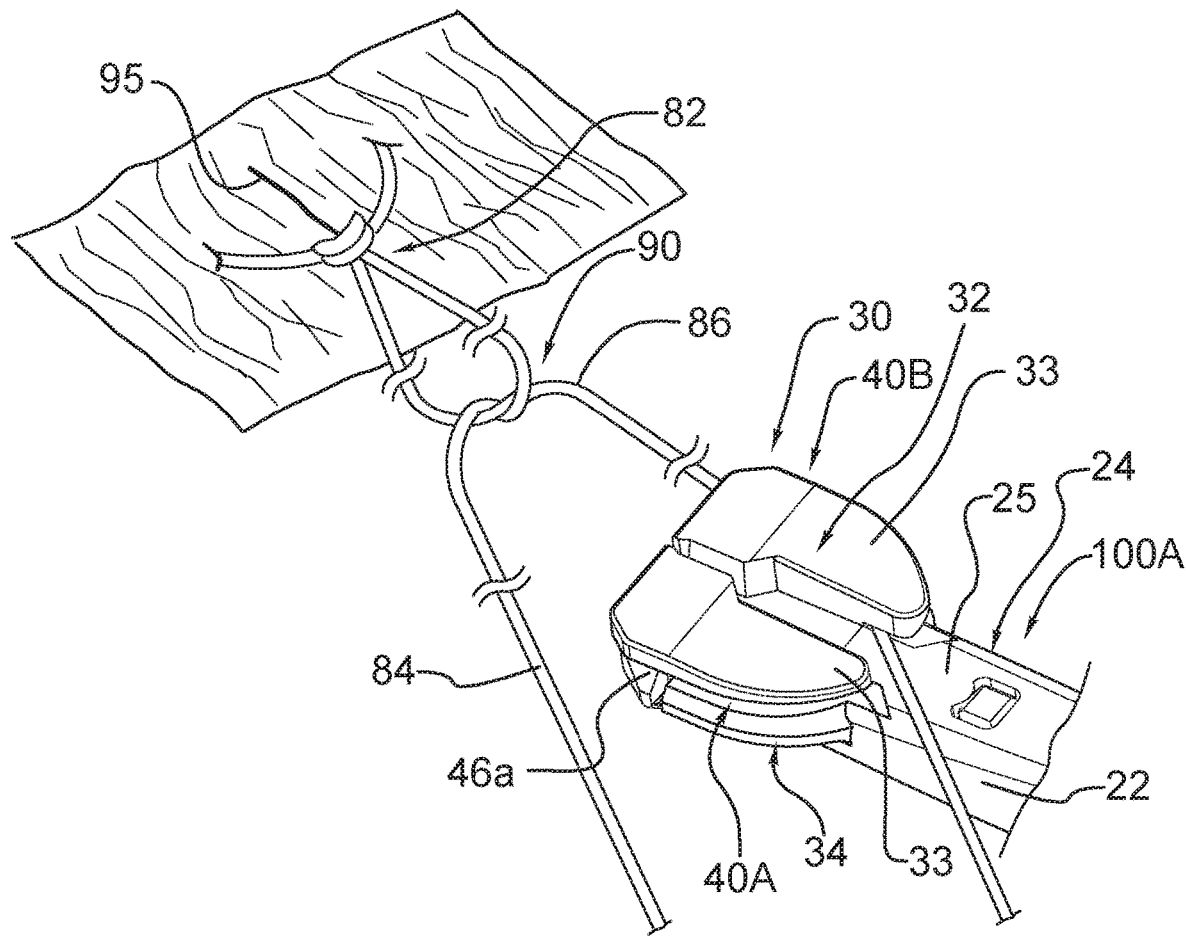

Following locking of the sliding knot, the physician may deploy one or more additional knots to further secure the sliding knot 82 in place. In one specific embodiment, one or more half-hitches or other overhand knots 90 may be formed and or deployed. These may then be advanced, using the knot pusher 100A, towards the tissue site having the defect 95. In one particular example, a half-hitch or overhand knot 90 is formed using the post 84 and the locker 86. The knot pusher 100A is placed directly behind the overhand knot 90. As shown in FIG. 7C, the knot pusher 100A is initially positioned such that one of the two strands of suture, such as the locker 86 is positioned against the top face of the neck 22 such that it rests against the tapered portion 24 thereof. As each of the opposed side grooves 40A and 40B are formed contiguously with the tapered portion 24, it allows each of the two strands of suture to be guided/lead into the into the side grooves 40A, 40B.

Figure 7D:
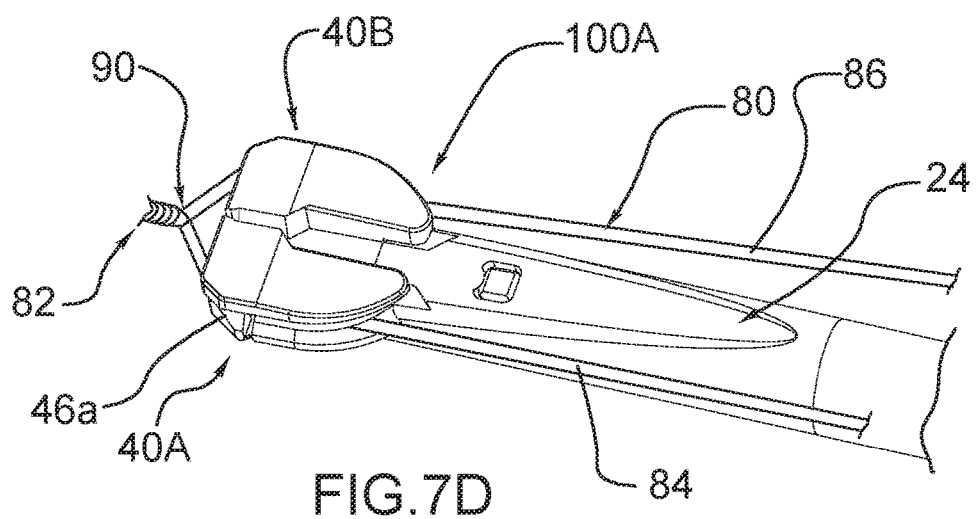

As shown in FIG. 7C, the flat planar surface 25 of the tapered portion 24 leads the locker 86 into the side groove 40B such that it rests between the top and bottom walls 32, 34. The knot pusher 100A may then be rotated, for example clockwise, to position the second strand of suture, such as the post 84, within the opposing side groove 40A, as shown in FIG. 7D. The flat planar surface 25 of the tapered portion 24 similarly aids in positioning of the post 84 within the side groove 40A. Thus, the tapered portion 24 facilitates loading of the suture strands within the knot pusher 100A to aid in the knot pushing procedure. Additionally, chamfered portions of the top and bottom walls 32, 34 also help guide the two suture strands (post 84, locker 86) within the two side grooves 40A, 40B. Additional features such as overhangs 33 of the top wall 32, allow each of the two strands of the suture 80 to be caught/secured within the side grooves 40A and 40B. The overhangs 33 allow the physician to hook the suture 80 into the side grooves 40A and 40B so that it engages with the knot pusher 100A. Thus, the overhangs 33 engage/capture the two suture strands prior to aid in guiding the two strands of suture within the side grooves 40A, 40B. This prevents the suture strands (post 84, locker 86) from falling out during transverse movement of the knot pusher 100A.

In some embodiments, the side grooves 40A, 40B have sufficient depth to retain the suture strands such as the post 84 and locker 86 when tension is maintained on the sutures. Additionally, in some embodiments a passive retention mechanism may be provided to retain the two strands of suture independently. In some such embodiments, for example where the suture strands such as the post 84 and locker 86 are passed through a pair of snaps such as snaps 46*a* and 46*b* (shown in FIGS. 2, 4B-4C) as they are guided into each of the side grooves 40A and 40B, the snaps function to retain the suture strands within these side grooves 40A, 40B. Additionally, chamfers on the snaps 46*a*, 46*b* may also aid in guiding suture 80 within the side grooves 40A, 40B.

The snaps 46*a*, 46*b* serve to constrain the sutures within the side grooves 40A and 40B even when tension is not maintained on the sutures. Therefore, the snaps 46*a* and 46*b* may help prevent the suture strands from disengaging from the knot pusher during, for example, patient movement or when tension is released from the suture strands in order to manipulate another instrument, and may thereby eliminate or reduce the need to reload the suture 80 into the knot pusher. As such, the snaps 46*a*, 46*b* may help reduce the time required for the knot pushing procedure.

Figure 7E:
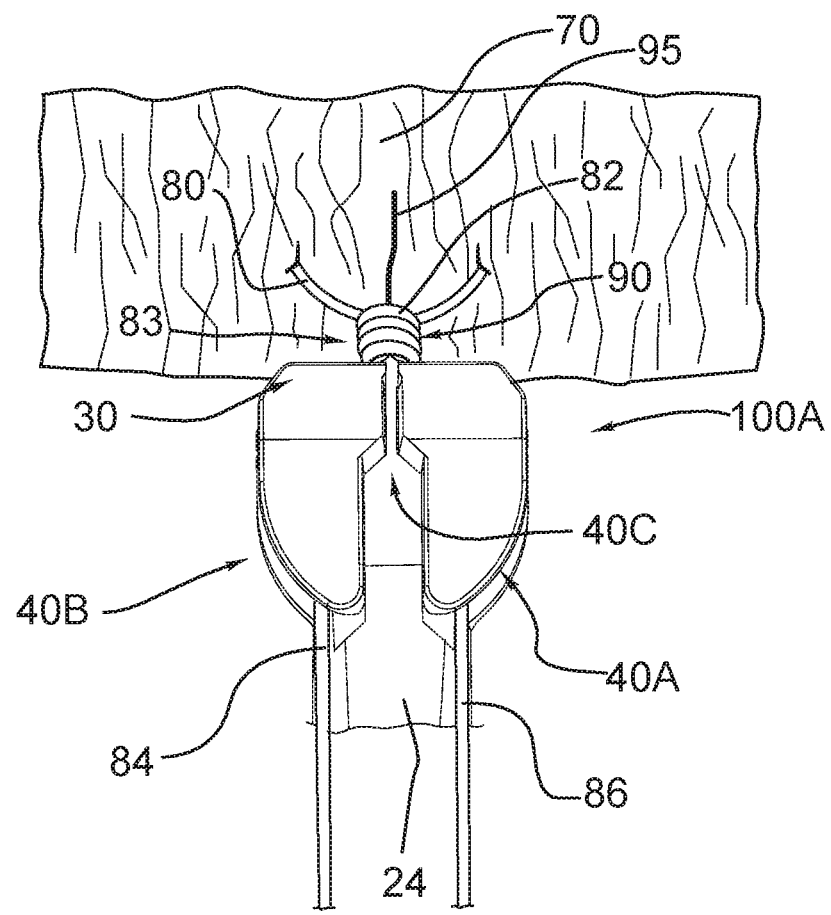

In some embodiments, the suture strands or limbs may be loaded onto the knot pusher 100A outside of the patient's body. After each strand of suture coming/deriving/extending from the overhand knot 90 has been placed within each of the respective side grooves 40A, 40B as shown in FIG. 7D, the knot pusher 100A is positioned directly behind the overhand knot 90. The knot pusher and the suture strands coupled thereto may then be advanced together into the patient's body to the target tissue surface. The knot pusher 100A is then advanced to push the overhand knot 90 towards the sliding knot 82. As the knot pusher 100A is advanced further, for example as shown in FIG. 7E, the knot pusher 100A functions to cinch the overhand knot 90 over top of the sliding knot 82 (such as the Dines knot 83).

The half-hitch or overhand knot 90 is centered between the side grooves 40A and 40B for securing the sliding knot 82. The central groove 40C' permits viewing of the overhand knot 90 as it is being advanced to ensure centering of the overhand knot so that equal tension is maintained on the two strands of sutures to guide the overhand knot on top of the sliding knot 82. Additionally, firm tension is maintained on the two suture strands, the post 84 and locker 86, as the knot pusher 100A is advanced. The knot pusher 100A may be pushed and retracted/released a plurality of times in order to tighten the half-hitch or overhand knot 90. In one specific example, the knot pusher 100A may be pushed and released four times to cinch the half-hitch or overhand knot 90. In some embodiments, four half-hitch or overhand knots 90 may be advanced towards the sliding knot 82 and tightened in order to secure the sliding knot 82 at the defect 95 within the tissue 70. Advancing and tightening four half-hitches or overhand knots provides an added advantage of preventing slipping or opening of the knot during loading conditions, as described further in the Examples below.

Figure 8:
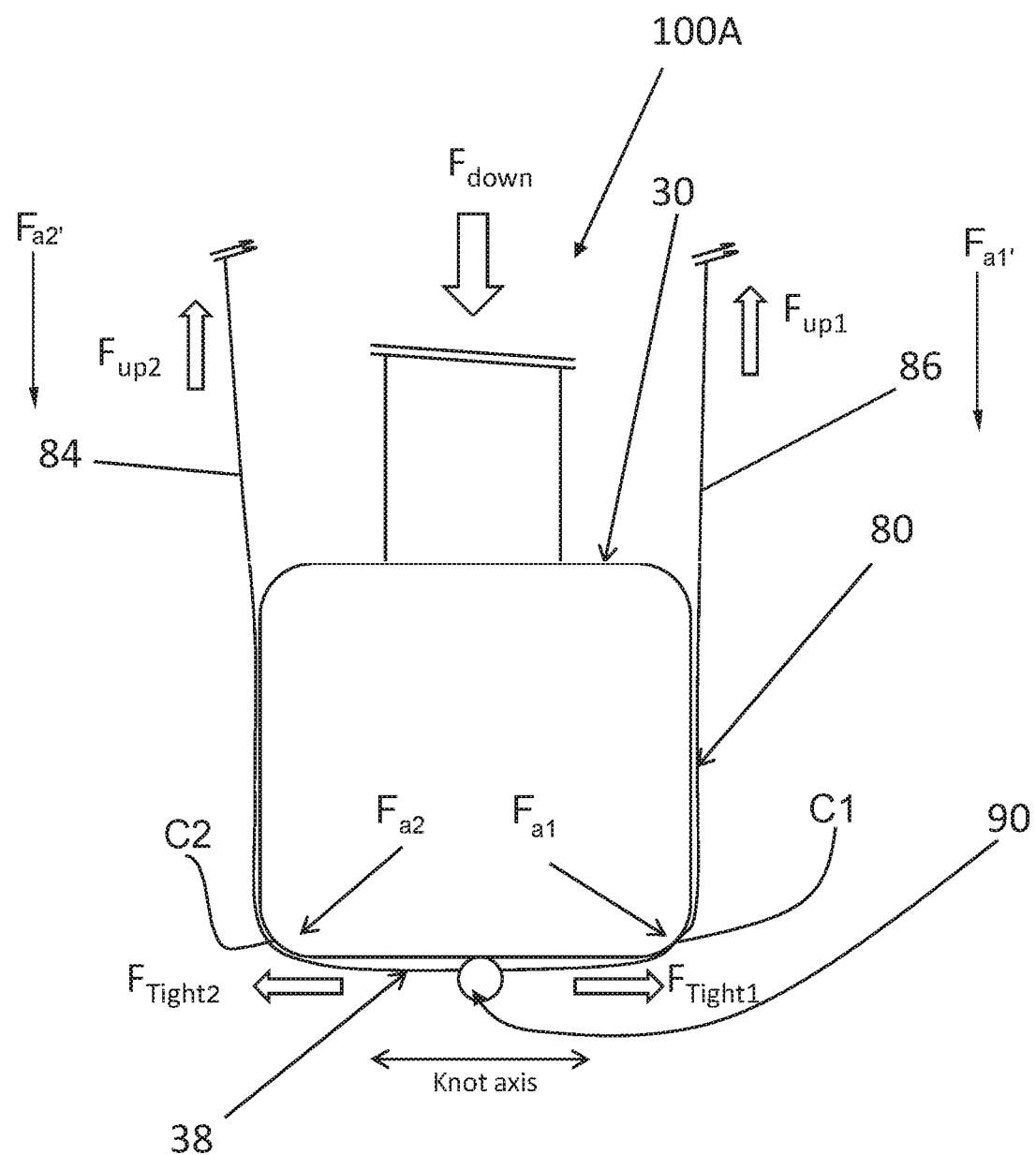
FIG. 8 schematically illustrates a distal head of a knot pusher and method of using the same, in accordance with an embodiment of the present invention.

The mechanism of pushing the overhand knot 90 is discussed further with reference to FIG. 8. A longitudinally directed force is applied by the user to the knot pusher 100A in a distal direction. This translates into a downward force ($F_{down}$) that is exerted by the distal head 30 against the suture strands (the post 84 and the locker 86). A portion of the knot pusher 100A, for example a curved or tapered portion of the side grooves (C1, C2), functions to translate a component of the applied force ($F_{down}$) which is substantially perpendicular to the suture strands at the distal face of the knot pusher into horizontal force components or tightening forces ($F_{tight1}$ and $F_{tight2}$) exerted against the portions of suture 80 that are substantially parallel to the distal face of the knot pusher.

More specifically, the downward force ($F_{down}$) results in an applied force ($F_{a1}$, $F_{a2}$) that is exerted on the suture strands by the distal head 30. The knot pusher 100A functions to translate a component of this applied force ($F_{a1}$, $F_{a2}$) into horizontal force components ($F_{tight1}$ and $F_{tight2}$) exerted against the suture 80. The knot pusher 100A also translates a component of the applied force ($F_{a1}$, $F_{a2}$) into vertical force components or downwards forces ($F_{a1'}$, $F_{a2'}$) that are exerted on the suture strands in a distal direction. Since the suture strands are held by the user, resistive forces ($F_{up1}$, $F_{up2}$) are exerted against the suture strands, which counteract the vertical force components ($F_{a1'}$, $F_{a2'}$) of the applied force ($F_{a1}$, $F_{a2}$). As such, the vertical components ($F_{a1'}$, $F_{a2'}$) of the applied force ($F_{a1}$, $F_{a2}$) are balanced by the resistive forces ($F_{up1}$, $F_{up2}$) whereas the parallel or horizontal force components ($F_{tight1}$ and $F_{tight2}$) of the applied force ($F_{a1}$, $F_{a2}$) continue to act in opposite directions on the suture strands extending from the overhand knot 90 to tighten the overhand knot 90. In other words, the counterbalancing of the horizontal force components ($F_{tight1}$ and $F_{tight2}$) allows tightening of the overhand knot 90. More specifically, the parallel force components ($F_{tight1}$ and $F_{tight2}$) function to spread the suture strands by about 180 degrees in order to tighten the overhand knot 90 against the tissue surface which it abuts.

Additionally, as the knot pusher 100A is advanced to tighten the overhand knot 90, the intermediate groove 40C is used as a central viewing channel to view the overhand knot 90 as it is being pushed towards and tightened on the target surface, for example as shown in FIG. 7E. This visual feedback enables centering of the overhand knot 90 to allow equal tension to be maintained on the two strands of suture in order to adequately position and tighten the overhand knot 90 onto the target surface as described hereinabove.

Example 1

The following tests were performed using a segment of porcine spine. A defect was made in a cervical disc, closed with a Dines knot as described hereinabove, and backed up with various amounts of half-hitch overhand knots. The degree or extent of knot slippage was observed after 1500N of compressive loading and 4000 cycles of flexion/extension after advancement of 2 half-hitches, 3 half-hitches and 4 half-hitches. Five samples for each of the knot constructs were observed. The average knot slippage observed for 2 half-hitches was about 8.8 mm, whereas the average knot slippage observed for 3 half-hitches was about 2.8 mm. However, for 4-half-hitches the inventors were surprised to observe that there was no knot slippage. This surprising and unexpected result was replicated under increased loading conditions. Knot slippage was observed for a 4 half-hitch knot construct after 1500N of compressive loading and 85000 cycles of flexion/extension. The average slippage was equal to about 0.8 mm. In conclusion, the inventors were surprised to observe that even under increased loading conditions, the four half-hitch knot construct substantially prevents knot slippage under normal loading conditions.

Example 2

In another example, force values were determined for slippage or breakage for a knot construct comprising a sliding knot in the form of a Dines knot that is backed up with 2, 3 or 4 half-hitches. Knot strength (defined as the force required to break the construct or to cause knot slippage) was determined to be 47 Newtons for 2 half-hitches, 75 Newtons for 3 half-hitches and 105 Newtons for 4-half-hitches. The mode of failure observed for the two half-hitch knots was slippage, whereas the mode of failure observed for the 4-half-hitches was predominantly breakage. This was a surprising and unexpected result further indicating that the four half-hitch knot construct is not prone to slippage. The breakage of the 4-half-hitches occurred under force conditions that exceed the forces generally seen at the site of a suture placed within a region of tissue within the body, such as the intervertebral disc. This further confirmed that 4-half-hitch knot construct is substantially resistant to slippage.

Thus, as described hereinabove, various embodiments of a knot pusher, and methods of use thereof, are disclosed. These embodiments provide a knot pusher operable to push or advance various types of knots, including sliding knots as well as overhand knots. Some such embodiments include an intermediate groove extending proximally from the knot pushing surface along the distal head, for holding one of the two strands of the suture forming a sliding knot, to allow the knot pusher to push the sliding knot. Embodiments of the knot pusher typically additionally have opposed side grooves for holding and guiding the two strands of the suture forming an overhand knot, to allow the knot pusher to push the overhand knot as well.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A knot pusher for pushing an overhand knot formed from a suture, two limbs of the suture extending from the knot, the knot pusher comprising:

a distal head defining top and bottom walls terminating in a distal knot pushing surface;

side grooves defined between said top and bottom walls, said side grooves extending proximally from said knot pushing surface along said distal head, each operable to receive one of the two limbs of suture during advancement of said distal head to aid in pushing said overhand knot; and at least one suture retaining element comprising a resilient suture retaining element for retaining a suture limb within at least one of said side grooves to prevent disengagement of said one of the suture limbs from the knot pusher during advancement of the distal head to push said overhand knot, the knot pusher further comprising a shaft coupled to the distal head and a handle coupled to the shaft;

wherein said distal head is coupled to the shaft via a neck portion, and wherein said at least one suture retaining element comprises a resilient snap arm is coupled to said neck portion, said snap arm forming a portion of one of said top and bottom walls.

2. The knot pusher of claim 1, wherein said resilient snap arm forms a portion of said top wall.

3. The knot pusher of claim 1, wherein said resilient snap arm forms a portion of said bottom wall.

4. The knot pusher of claim 1, wherein said resilient snap arm comprises a pair of resilient snaps, each of said pair of resilient snaps defining a portion of one of said side grooves.

5. The knot pusher of claim 1, wherein said resilient snap arm is coupled to said neck portion via a snap fit.

6. The knot pusher of claim 4, wherein each of said pair of resilient snaps comprises a chamfered surface to facilitate entry of a respective one of the two suture limbs within a corresponding one of said side grooves.

7. The knot pusher of claim 1, wherein said top wall comprises a top wall suture receiving element for receiving one of the two suture limbs during advancement of said distal head to facilitate advancement of a sliding knot.

8. The knot pusher of claim 7, wherein said top wall suture receiving element comprises an intermediate groove formed within said top wall between said side grooves, said intermediate groove extending proximally from said knot pushing surface longitudinally along said distal head.

9. The knot pusher of claim 8, wherein said intermediate groove comprises a central groove.

10. The knot pusher of claim 8, wherein said intermediate groove extends along a longitudinal axis of the distal head that is parallel to and offset from the central axis, forming an offset groove.

11. The knot pusher of claim 8, wherein the intermediate groove suture retaining element comprises one or more resilient snap arms to retain said one of the two limbs of suture within the intermediate groove.

12. The knot pusher of claim 1, wherein the distal head comprises markings thereon indicating desired placement of the suture limbs to facilitate advancement of the sliding knot.

13. The knot pusher of claim 7, further comprising a tensioning aid positioned along the shaft for maintaining tension on the one of the two suture limbs received within the top wall suture receiving element.

14. The knot pusher of claim 8, wherein said central groove is located along a central axis of said knot pusher and forms a visualization channel to permit visual centering of said overhand knot during advancement of the distal head to push said overhand knot.

15. The knot pusher of claim 8, wherein the distal portion of said central groove is sufficiently narrow for preventing said knot from slipping into said central groove as the distal head is advanced to push said sliding knot.

16. The knot pusher of claim 1, wherein said knot pushing surface is oriented at an angle of less than about 90 degrees from a plane defined by the top wall of the knot pusher.

17. The knot pusher of claim 1, wherein the distal knot pushing surface is substantially flat along its width.

18. The knot pusher of claim 1, wherein the distal head is offset from the handle to permit visualization of the distal head when the handle is being held.

19. The knot pusher of claim 1, wherein a proximal portion of said top wall forms an overhang for guiding each of the two suture limbs into the side grooves.

20. The knot pusher of claim 1, wherein said side grooves are spaced apart by a distance substantially equal to the width of each of said side grooves.

* * * * *